US011291850B2

(12) United States Patent
Pavel et al.

(10) Patent No.: US 11,291,850 B2
(45) Date of Patent: Apr. 5, 2022

(54) SYSTEMS FOR MEDICAL DEVICE INTERACTIONS

(71) Applicant: ZOLL MEDICAL CORPORATION, Chelmsford, MA (US)

(72) Inventors: Trisha A. Pavel, Pittsburgh, PA (US); John G. Clark, Pittsburgh, PA (US); Edward J. Donnelly, Allison Park, PA (US); Thomas E. Kaib, Irwin, PA (US)

(73) Assignee: ZOLL MEDICAL CORPORATION, Chelmsford, MA (US)

( * ) Notice: Subject to any disclaimer, the term of this patent is extended or adjusted under 35 U.S.C. 154(b) by 203 days.

(21) Appl. No.: 16/803,231

(22) Filed: Feb. 27, 2020

(65) Prior Publication Data

US 2020/0188683 A1 Jun. 18, 2020

Related U.S. Application Data

(63) Continuation of application No. 15/217,132, filed on Jul. 22, 2016, now Pat. No. 10,617,881.
(Continued)

(51) Int. Cl.
*A61N 1/39* (2006.01)
*A61B 5/00* (2006.01)
(Continued)

(52) U.S. Cl.
CPC .......... *A61N 1/3987* (2013.01); *A61B 5/0205* (2013.01); *A61B 5/339* (2021.01); *A61B 5/4836* (2013.01); *A61B 5/4875* (2013.01); *A61B 5/6831* (2013.01); *A61B 7/02* (2013.01); *A61N 1/046* (2013.01); *A61N 1/0456* (2013.01);
(Continued)

(58) Field of Classification Search
CPC .............. A61N 1/3987; A61N 1/36031; A61N 1/0456; A61N 1/046; A61N 1/0484; A61N 1/36014; A61N 1/3625; A61N 1/36514; A61N 1/36542; A61N 1/3993; A61B 5/339; A61B 5/0205; A61B 5/4836; A61B 5/4875; A61B 5/6831; A61B 7/02;
(Continued)

(56) References Cited

U.S. PATENT DOCUMENTS 6,980,112 B2 12/2005 Nee
7,974,689 B2 7/2011 Volpe et al.
(Continued)

*Primary Examiner* — Erin M Piateski
(74) *Attorney, Agent, or Firm* — Lando & Anastasi, LLP

(57) ABSTRACT

An external wearable medical device includes an electrode to detect patient cardiac activity; a therapy electrode to provide a therapy in response to detecting an arrhythmia event; a GUI display comprising a caregiver interface and a patient interface; and a processor configured to provide, to the caregiver interface, a first set of information that includes information for operating the device in conjunction with the patient and an alert history of the device including an indication of one or more detected arrhythmia events, provide, to the patient interface, a second set of information that includes information for allowing the patient to cause the device to suspend providing the therapy and a direction to the patient to contact a caregiver responsive to detecting an event affecting at least one of the device and the patient, and responsive to detecting the event, automatically transmitting a notification of the event to an external entity.

20 Claims, 20 Drawing Sheets

Related U.S. Application Data

(60) Provisional application No. 62/195,696, filed on Jul. 22, 2015.

(51) Int. Cl.

| | | |
|---|---|---|
| *A61N 1/365* | (2006.01) | |
| *A61N 1/36* | (2006.01) | |
| *A61N 1/362* | (2006.01) | |
| *A61N 1/04* | (2006.01) | |
| *A61B 7/02* | (2006.01) | |
| *A61B 5/0205* | (2006.01) | |
| *A61B 5/044* | (2006.01) | |
| *A61B 5/339* | (2021.01) | |
| *A61B 5/08* | (2006.01) | |
| *A61B 7/00* | (2006.01) | |
| *A61B 5/11* | (2006.01) | |
| *A61B 5/25* | (2021.01) | |

(52) U.S. Cl.
CPC ....... *A61N 1/0484* (2013.01); *A61N 1/36014* (2013.01); *A61N 1/3625* (2013.01); *A61N 1/36031* (2017.08); *A61N 1/36514* (2013.01); *A61N 1/36542* (2013.01); *A61N 1/3993* (2013.01); *A61B 5/08* (2013.01); *A61B 5/1118* (2013.01); *A61B 5/25* (2021.01); *A61B 7/003* (2013.01); *A61B 2560/0276* (2013.01); *A61B 2560/0431* (2013.01)

(58) Field of Classification Search
CPC .......... A61B 5/25; A61B 5/08; A61B 5/1118; A61B 7/003; A61B 2560/0276; A61B 2560/0431
USPC ............................................................ 607/6
See application file for complete search history.

(56) References Cited

U.S. PATENT DOCUMENTS

| | | | |
|---|---|---|---|
| 8,140,154 B2 | 3/2012 | Donnelly et al. | |
| 8,644,925 B2 | 2/2014 | Volpe et al. | |
| 8,903,487 B1* | 12/2014 | Fischell | A61B 5/366 |
| | | | 607/9 |
| 8,983,597 B2 | 3/2015 | Whiting et al. | |
| 9,007,216 B2 | 4/2015 | Oskin et al. | |
| 9,008,801 B2 | 4/2015 | Kaib et al. | |
| 9,135,398 B2 | 9/2015 | Kaib et al. | |
| 9,579,516 B2 | 2/2017 | Kaib et al. | |
| 9,597,523 B2 | 3/2017 | Kaib et al. | |
| 9,737,701 B2 | 8/2017 | Dupelle et al. | |
| 2003/0004547 A1* | 1/2003 | Owen | A61N 1/046 |
| | | | 607/5 |
| 2006/0189900 A1* | 8/2006 | Flaherty | G06N 3/061 |
| | | | 600/595 |
| 2007/0239214 A1 | 10/2007 | Cinbis | |
| 2011/0022105 A9 | 1/2011 | Owen et al. | |
| 2012/0112903 A1 | 5/2012 | Kaib et al. | |
| 2013/0231711 A1* | 9/2013 | Kaib | G16H 80/00 |
| | | | 607/5 |
| 2013/0325096 A1 | 12/2013 | Dupelle et al. | |
| 2014/0012346 A1* | 1/2014 | Gilkerson | A61N 1/36514 |
| | | | 607/20 |
| 2014/0025131 A1 | 1/2014 | Sullivan et al. | |
| 2014/0206977 A1 | 7/2014 | Bahney et al. | |
| 2015/0359490 A1* | 12/2015 | Massey | A61B 5/7207 |
| | | | 600/365 |
| 2016/0004831 A1 | 1/2016 | Carlson et al. | |
| 2016/0278659 A1 | 9/2016 | Kaib et al. | |
| 2016/0303371 A1 | 10/2016 | Whiting et al. | |
| 2017/0021184 A1 | 1/2017 | Pavel et al. | |
| 2017/0056682 A1 | 3/2017 | Kumar et al. | |

\* cited by examiner

SYSTEMS FOR MEDICAL DEVICE INTERACTIONS

RELATED APPLICATIONS

This application claims the benefit under 35 U.S.C. § 120 as a continuation of U.S. application Ser. No. 15/217,132, filed Jul. 22, 2016, titled SYSTEMS FOR MEDICAL DEVICE INTERACTIONS, which claims priority under 35 U.S.C. § 119(e) to U.S. Provisional Application Ser. No. 62/195,696, filed Jul. 22, 2015, titled MEDICAL DEVICE INTERACTIONS, each of which is hereby incorporated herein by reference in its entirety for all purposes.

BACKGROUND

Technical Field

This disclosure relates to systems and techniques for facilitating human interactions with medical devices, in particular caregiver and patient interactions with external medical devices.

Discussion

There are a wide variety of electronic and mechanical devices for monitoring and treating patients' medical conditions. In some examples, depending on the underlying medical condition being monitored or treated, medical devices such as cardiac pacemakers or defibrillators may be surgically implanted or connected externally to the patient. In some cases, physicians may use medical devices alone or in combination with drug therapies to treat patient medical conditions.

One of the most deadly cardiac arrhythmias is ventricular fibrillation, which occurs when normal, regular electrical impulses are replaced by irregular and rapid impulses, causing the heart muscle to stop normal contractions and to begin to quiver. Normal blood flow ceases, and organ damage or death can result in minutes if normal heart contractions are not restored. Because the victim has no perceptible warning of the impending fibrillation, death often occurs before the necessary medical assistance can arrive. Other cardiac arrhythmias can include excessively slow heart rates known as bradycardia.

Implantable or external pacemakers and defibrillators (such as automated external defibrillators or AEDs) have significantly improved the ability to treat these otherwise life-threatening conditions. Such devices operate by applying corrective electrical pulses directly to the patient's heart. For example, bradycardia can be corrected through the use of an implanted or external pacemaker device. Ventricular fibrillation can be treated by an implanted or external defibrillator.

For example, certain medical devices operate by continuously or substantially continuously monitoring the patient's heart through one or more sensing electrodes for treatable arrhythmias and, when such is detected, the device applies corrective electrical pulses directly to the heart through one or more therapy electrodes.

SUMMARY

According to at least one aspect, an external medical device is provided. The external medical device includes one or more electrodes configured to detect a cardiac activity of the patient, a treatment component configured to provide a therapy to the patient based at least in part on the cardiac activity detected by the electrodes, a user interface including at least one caregiver interface and at least one patient interface, and a processor in communication with the user interface. The processor may be configured to a first set of information to the caregiver interface and a second set of information to the patient interface. In some examples, the first set of information includes information for operating the external medical device in conjunction with the patient and the second set of information includes information for allowing the patient to cause the external medical device to suspend providing the therapy to the patient.

In some examples, the first set of information includes a notification including a direction to the caregiver to administer at least one training module to the patient. In some examples, the first set of information includes device-guided instructions for setting up the device for use in conjunction with the patient.

In some examples, the processor is further configured to cause the user interface to prompt for security credentials before providing access to the caregiver interface. In some examples, the second set of information further includes a notification including a direction to the patient to contact a healthcare provider responsive to detecting an event.

In some examples, the first and second sets of information includes at least one of notifications, instructions, directions, prompts, messages, alerts, device status information, and patient-related information. In some examples, the first and second information can be provided through at least one of a visual, audible, tactile, or Braille output component.

According to at least one aspect, an external medical device is provided. The external medical device includes a sensing component configured to attach to a patient and detect a cardiac activity of the patient, a treatment component configured to provide a therapy to the patient based at least in part on the detected cardiac activity of the patient from the sensing component, and a controller including an output component. The controller may be configured to provide access to at least one training module relating to an operation of the external medical device and provide a notification via the output component to administer the at least one training module.

In some examples, the sensing component is configured to detect at least one of ECG activity, tissue fluid, lung fluid, lung sounds, heart sounds, and patient activity. In some examples, the treatment component includes a therapy electrode for providing at least one of a defibrillating, pacing and transcutaneous electrical nerve stimulation (TENS) therapy to the patient. In some examples, the notification includes direction to a caregiver to administer the at least one training module to the patient.

In some examples, the notification includes direction to a caregiver to review the at least one training module. In some examples, the notification includes direction to the patient to review the at least one training module.

In some examples, the at least one output component includes a display and wherein the controller provides the notification via the display. In some examples, the at least one output component includes a visual indicator and wherein the controller provides the notification via the visual indicator. In some examples, the at least one output component includes a speaker, and wherein the controller provides the notification as an audible alert via the speaker.

In some examples, the at least one training module includes at least one of: a bystander training module, a patient training module, and a caregiver training module. In some examples, the at least one training module includes at least one of: a response button training module, a garment training module, and a device action training module.

In some examples, the controller provides the notification responsive to detecting an event. The event may include, for example, at least one of: connecting the sensing component to the controller, initiation of communication between the sensing component and the controller, connecting a battery to the controller, a predetermined period of time elapsing, detecting that the at least training module has not been accessed, and fitting the external medical device to a patient. In at least one example, the event of fitting the external medical device to a patient may include causing the device to enter a new patient mode.

In some examples, the controller monitors a completion status of the at least one training module and provides the notification in response to the completion status.

In some examples, the at least one training module includes a plurality of sections and the controller suppresses the notification responsive to a predetermined minimum number of sections of the plurality of sections being completed. The controller may be configured to monitor a duration of access of each section of the plurality of sections and identify the respective each section of the plurality of sections as complete responsive to the duration of access exceeding a second completion threshold.

In some examples, the controller is configured to monitor a duration of access of the at least one training module and identify the at least one training module as incomplete responsive to the duration of access to the at least one training module being below a module completion threshold. In some examples, the controller includes a network interface, the controller configured to transmit a message to an external system via the network interface, the message relating to at least one of the patient and the external medical device.

In some examples, the controller includes at least one input device, the controller configured to override the notification responsive to receiving user input via the at least one input device. In some examples, the at least one input device includes at least one of a touch screen and a keypad, and wherein the user input includes one or more security credentials.

In some examples, the controller is configured to send a signal to an external system in response to providing the notification. In some examples, the notification includes a training access feature configured to, responsive to user input, provide access to the at least one training module. In some examples, the external medical device is configured to attach to the patient via adhesive electrodes. In some examples, the external medical device is configured for long term attachment to the patient.

In some examples, the sensing component is configured for long term monitoring of the patient. In some examples, the external medical device is configured for substantially continuous attachment to the patient. In some examples, the sensing component is configured for substantially continuous monitoring of the patient.

According to at least one aspect, an external medical device is provided. The external medical device includes a plurality of electrodes configured to attach to a patient, the plurality of electrodes including at least one cardiac sensing electrode and at least one therapy electrode and a controller unit coupled to the plurality of electrodes and including at least one output device. The controller unit may be configured to administer at least one training module and provide a notification via the at least one output device, the notification including a direction to a caregiver to administer the at least one training module to the patient.

In some examples, the at least one output device includes a display and wherein the controller unit is configured to provide the notification to the caregiver via the display. In some examples, the at least one training module includes at least one of: a pacing training module, a defibrillation training module, and an arrhythmia detection training module.

In some examples, the controller unit is configured to provide the notification responsive to detecting an event. The event may include, for example, at least one of: connecting the plurality of electrodes to the controller unit, connecting a battery to the controller unit, a predetermined period of time elapsing, and fitting the external medical device to a new patient.

In some examples, the controller unit is configured to monitor a completion status of the at least one training module and provide the notification to the caregiver responsive to the completion status of the at least one training module being incomplete.

In some examples, the at least one training module includes a plurality of sections and wherein the controller unit is configured to suppress the notification to the health care provider responsive to a minimum number of sections of the plurality of sections being completed. The controller unit may be configured to monitor a duration of access of each section of the plurality of sections and identify the respective section as complete responsive to the duration of access to the respective section exceeding a threshold.

In some examples, the controller unit is configured to monitor a duration of access of the at least one training module and determine that the administration of the at least one training module was rushed responsive to the duration of access to the at least one training module being below a threshold. The controller unit may include a network interface and is configured to transmit a message to an external system via the network interface indicating that the administration of the at least one training module was rushed.

In some examples, the controller unit includes at least one input device and wherein the controller unit is configured to override the notification responsive to receiving input from the caregiver via the at least one input device. The at least one input device may include, for example, at least one of a touch screen and a keypad and wherein the input from the caregiver includes one or more security credentials.

In some examples, the external medical device is a hospital worn device and wherein the caregiver includes a trained medical service provider. The trained medical service provider may include, for example, at least one of a nurse, a physician assistant, and a doctor.

According to at least one aspect, a patient monitoring device is provided. The patient monitoring device includes a sensing component configured to attach to a patient and detect one or more parameters relating to the patient and a controller including an output component. The controller may be configured to administer at least one training module and provide a notification via the output component to administer the at least one training module. It is appreciated that the sensing component, in some examples, may be configured to detect cardiac activity of the patient.

According to at least one aspect, an external medical device is provided. The external medical device includes a plurality of electrodes configured to attach to a patient including at least one cardiac sensing electrode and at least one therapy electrode and a controller in communication with the plurality of electrodes. The controller may be configured to detect an event associated with at least one of the external medical device and the patient and provide a notification via at least one output component, the notification including a direction to the patient to contact a caregiver.

In some examples, the controller unit includes at least one response mechanism and the controller detects an arrhythmia of the patient, instructs the patient to operate the at least one response mechanism, and provides the notification to the patient to contact the caregiver responsive to operation of the at least one response mechanism. The controller may, for example, delay treatment to the patient via the at least one therapy electrode and provides a notification to the patient that treatment is being delayed responsive to operation of the at least one response mechanism. In some examples, the at least one output component includes a display and the controller unit may, for example, alternate between displaying a notification to the patient to contact the caregiver and displaying a notification to the patient that treatment is being delayed.

In some examples, the at least one output component includes a display and wherein the controller unit displays a notification to the patient to contact the caregiver.

In some examples, the controller unit detects at least one malfunction of the external medical device and provides a notification to the patient to contact the caregiver responsive to detecting the at least one malfunction. The at least one malfunction may include, for example, at least one of electrode falloff, excessive noise, and low battery.

In some examples, the controller unit automatically contacts the caregiver responsive to operation of the at least one response mechanism. In some examples, the controller unit automatically contacts the caregiver responsive to detection of an arrhythmia.

In some examples, the external medical device is a hospital worn device and wherein the caregiver includes a trained medical service provider. The trained medical service provider may include, for example, at least one of a nurse, a physician assistant, and a doctor.

Other features and advantages of the invention will be apparent from the drawings, detailed description, and claims. Moreover, it is to be understood that both the foregoing information and the following detailed description are merely illustrative examples of various aspects, and are intended to provide an overview or framework for understanding the nature and character of the claimed subject matter. Any example disclosed herein may be combined with any other example. References to "an example," "some examples," "an alternate example," "various examples," "one example," "at least one example," "this and other examples" or the like are not necessarily mutually exclusive and are intended to indicate that a particular feature, structure, or characteristic described in connection with the example may be included in at least one example. The appearance of such terms herein is not necessarily all referring to the same example.

Furthermore, in the event of inconsistent usages of terms between this document and documents incorporated herein by reference, the term usage in the incorporated references is supplementary to that of this document; for irreconcilable inconsistencies, the term usage in this document controls. In addition, the accompanying drawings are included to provide illustration and a further understanding of the various aspects and examples, and are incorporated in and constitute a part of this specification. The drawings, together with the remainder of the specification, serve to explain principles and operations of the described and claimed aspects and examples.

BRIEF DESCRIPTION OF DRAWINGS

The accompanying drawings are not intended to be drawn to scale. In the drawings, components that are identical or nearly identical may be represented by a like numeral. For purposes of clarity, not every component is labeled in every drawing. In the drawings.

DETAILED DESCRIPTION

Figure 1:
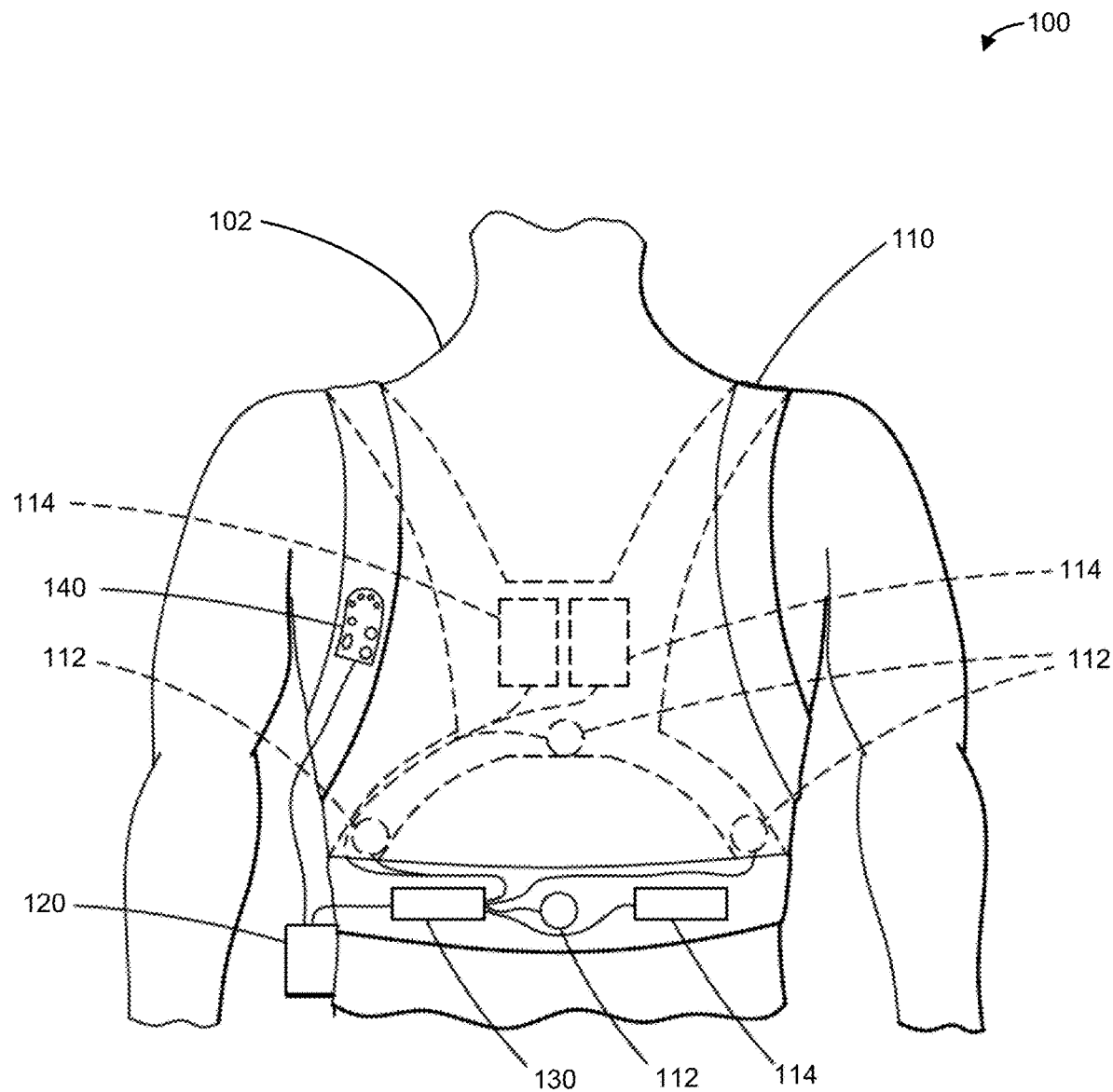
FIG. 1 shows an example wearable defibrillator.

Systems and techniques as disclosed herein are provided to facilitate and manage human interactions with medical devices. For example, medical devices as disclosed herein may be cardiac devices that monitor one or more cardiac signals of a patient. For example, such medical devices can be configured to determine whether the patient may be experiencing a cardiac condition. The medical devices can include a plurality of sensing electrodes that are disposed at one or more locations of the patient's body and configured to detect or monitor the cardiac signals of the patient. In some implementations, the medical device can be configured to monitor, in addition to cardiac signals, other physiological parameters as described in further detail below. For example, such devices can be used as cardiac monitors in certain cardiac monitoring applications, such as mobile cardiac telemetry (MCT) and/or continuous event monitoring (CEM) applications.

In some implementations, a medical device as disclosed herein can be configured to determine an appropriate treatment for the patient based on the detected cardiac signals (and/or other physiological parameters) and cause one or more therapeutic shocks (e.g., defibrillating and/or pacing shocks) to be delivered to the body of the patient as described in further detail below. Accordingly, the medical device can include one or more therapy electrodes that are disposed at one or more locations of the patient's body and configured to deliver the therapeutic shocks.

A medical device as described herein can be configured to monitor a patient for a cardiac arrhythmia condition such as bradycardia, ventricular tachycardia (VT) or ventricular fibrillation (VF). In addition, while the detection methods and systems described hereinafter are disclosed as detecting VT and VF, this is not to be construed as limiting the invention as other arrhythmias, such as, but not limited to, atrial arrhythmias such as premature atrial contractions (PACs), multifocal atrial tachycardia, atrial flutter, and atrial fibrillation, supraventricular tachycardia (SVT), junctional arrhythmias, tachycardia, junctional rhythm, junctional tachycardia, premature junctional contraction, and ventrical arrhythmias such as premature ventricular contractions (PVCs) and accelerated idioventricular rhythm, may also be detected. In the case of treatment devices, such as, pacing and/or defibrillating devices, if an arrhythmia condition is detected, the device can automatically provide a pacing, defibrillation, and/or transcutaneous electrical nerve stimulation (TENS) pulses or shocks, as needed, to treat the condition.

Aspects of the present disclosure manifest an appreciation for various challenges in deploying a medical device in a busy hospital environment. For example, a single medical device may be used on multiple patients in succession and require a caregiver (e.g., a nurse or other medical practitioner) to setup and/or configure the medical device for each patient that is prescribed the medical device. A caregiver may include, for example, a medically trained professional, such as a physician, physician assistant, or nurse. In addition, a busy nurse or other caregiver in a hospital may provide a medical device to a bedridden patient without providing the patient any guidance as to the appropriate ways to interact with the medical device. These patients may, consequently, believe that they should not touch or interact with the medical device regardless of the alarms being issued or contact a caregiver should any issue arise with the device (or medical condition of the patient). The lack of communication by the patient to the caregiver regarding events experienced by the patient may cause long delays between an event occurring (e.g., a patient experiences an arrhythmia) and the caregiver being notified.

The medical device as disclosed herein in some examples is capable of providing a first set of information directed to a caregiver of the patient (e.g., via a caregiver interface) and a second set of information directed to the patient (e.g., via a patient interface), or in some circumstances a guardian of the patient, such as a family member who is typically not medically trained. In a hospital setting, for example, the medical device may communicate with a nurse through a caregiver interface to help the nurse setup, configure, and/or operate the medical device for the patient. The information directed to the caregiver may require entry of one or more security credentials (e.g., username and password) to, for example, restrict the patient from accessing the caregiver interface. The medical device may also issue various alerts, alarms, and/or messages to the patient to instruct the patient on device operation, how to delay the administration of therapy through a patient interface should the patient be conscious, etc.

In some examples, the first and second sets of information directed to the caregiver and/or the patient may include various training modules. These training modules may include, for example, training modules for the caregiver to administer to the patient (e.g., training modules for the caregiver to step through with the patient). For example, the training modules may include one or more modules to train the patient on the sequence of events that may be encountered by the patient prior to treatment being applied. It is appreciated that the training modules may be directed to the patient and/or the caregiver personally. For example, the training modules may include a showering training module to train the caregiver on the appropriate way to shower the patient with the medical device. In other implementations, the training modules can be directed to other personnel (e.g., patient service representatives) involved in the deployment of the medical device.

The medical device may issue various reminders to the caregiver and/or the patient to complete various training modules. For example, the medical device may remind the caregiver to administer training to the patient upon initialization of the medical device and/or detection of an event (e.g., connecting a battery to the medical device). The medical device may provide reminders until the appropriate training has been completed.

In some examples, the medical device provides a notification for the patient to contact a caregiver responsive to detecting an event. For example, the medical device may provide treatment to the patient and instruct the patient to contact a caregiver. Other example events that may trigger a notification to the patient to contact a caregiver include detecting a malfunction of the medical device, an error condition, detecting an arrhythmia, and delaying treatment of the arrhythmia. These notifications to the patient remind the patient to contact a caregiver to make the healthcare provider aware of any changes in the medical condition of the patient and/or the condition of the medical device.

In various implementations described herein, the information directed to a user and/or audience can include notifications that are directed according to one or more roles of the user and/or the audience. For example, the information or notifications can be one or more directions to a caregiver as described herein and as such include one or more of audio output, tactile output (e.g., vibration alerts or feedback), Braille output, and/or visual output such as text, graphics, video, animations and/or other information conveying features directed at the caregiver. Similarly, information or notifications directed to a patient as described herein can include one or more of audio output, tactile output, Braille output, and/or visual output such as text, graphics, video, animations and/or other information conveying features directed at the patient. Information or notifications directed to a patient service representative or a technical service person as described herein can include one or more of audio output, tactile output, Braille output, and/or visual output such as text, graphics, video, animations and/or other information conveying features directed at the patient service representative or the technical service person. As described herein, the one or more notifications can further include user input features for receiving a user's response to the one or more notifications. For example, a patient can respond to a voice or video notification by speaking a command. For example, a patient may be able to respond to a visual notification by touching a user interface screen or pushing one or more physical or user interface buttons.

Example Medical Devices

In some implementations, the medical device as described herein is an external or non-invasive medical device (e.g., in contrast to internal or invasive devices, such as implantable medical devices). For example, the external medical device can be a cardiac monitoring and/or automated pacing device or defibrillator, such as an in-facility continuous monitoring defibrillator (e.g., for patients that are confined to a limited space within a facility, such as, within a hospital environment, to a patient's room) or outpatient wearable defibrillators.

In some implementations, an external medical device can be an automated cardiac monitor or defibrillator that can be used in certain specialized conditions and/or environments such as in combat zones or within emergency vehicles. The medical device can be configured so that it can be used immediately (or substantially immediately) in a life-saving emergency. For example, the external medical device can be an automated external defibrillator (AED). Such AEDs are available from ZOLL® Medical Corporation of Chelmsford, Mass.

In some implementations, the external medical device is an ambulatory device (e.g., a device that is capable of and designed for moving with the patient as the patient goes about his or her daily routine). In some examples, the external medical device can be configured as a wearable defibrillator, such as the LifeVest® wearable defibrillator available from ZOLL® Medical Corporation of Chelmsford, Mass.

The devices as described herein may be capable of continuously, substantially continuously, long-term and/or extended use or wear by, or attachment or connection to a patient.

For example, devices as described herein may be capable of being used or worn by, or attached or connected to a patient, without substantial interruption for a predetermined period of time. In some examples, such devices may be capable of being used or worn by, or attached or connected to a patient for example, up to hours or beyond (e.g., weeks, months, or even years).

In some implementations, such devices may be removed for a period of time before use, wear, attachment, or connection to the patient is resumed, e.g., to change batteries, to change or wash the garment, and/or to take a shower, without departing from the scope of the examples described herein.

The devices as described herein may be capable of continuously, substantially continuously, long-term and/or extended monitoring of a patient.

For example, devices as described herein may be capable of providing cardiac monitoring without substantial interruption for a predetermined period of time. In some examples, such devices may be capable of continuously or substantially continuously monitoring a patient for cardiac-related information (e.g., ECG information, including arrhythmia information, heart sounds, etc.) and/or non-cardiac information (e.g., blood oxygen, the patient's temperature, glucose levels, and/or lung sounds), for example, up to hours or beyond (e.g., weeks, months, or even years).

In some implementations, such devices may be powered down for a period of time before monitoring is resumed, e.g., to change batteries, to change or replace the garment, and/or to take a shower, without departing from the scope of the examples described herein.

In some instances, the devices may carry out its monitoring in periodic or aperiodic time intervals or times. For example, the monitoring during intervals or times can be triggered by a user action or another event. For example, one or more durations between the periodic or aperiodic intervals or times can be user-configurable.

In various implementations, the devices may be operated on battery power for a duration of the device's use after which the batteries may be replaced and/or recharged.

In some implementations, the medical device as described herein can be a hospital based medical device including, for example, a cardiac monitoring device, a defibrillator and/or pacing device. For example, such a hospital based device can include a defibrillator and/or pacing device configured for continuous or substantially continuous use, wear, connection, attachment, or monitoring to/of a patient in a hospital environment. The hospital based device can include a plurality of therapy and sensing electrodes that are attached to the patient's skin. In some examples, the sensing and/or therapy electrodes are disposable adhesive electrodes. In some implementations, the electrodes are affixed to an electrode assembly (a patch), which can then be adhesively attached to the patient's skin. The sensing and/or therapy electrodes can be attached to the patient's skin at particular locations as prescribed by a trained professional.

In some implementations, the medical device as described herein can be configured to monitor a patient presenting with syncope (e.g., by analyzing the patient's cardiac activity for aberrant patterns that can indicate abnormal physiological function). In some examples, aberrant patterns may occur prior to, during, or after the onset of syncope symptoms. For example, the short-term outpatient defibrillator can include a plurality of electrodes and/or an electrode assembly (patch) that can be adhesively attached to the patient's skin. The patient may replace the electrodes and/or patches as prescribed.

For example, the medical device can include a user interface component for interacting with the medical device. For example, the user interface component can include at least one caregiver interface and at least one patient interface. The device can include one or more input mechanisms (e.g., buttons) that are available via the patient interface so that the patient can interact with the device to respond to a treatment alert. In some examples, the medical device issues a treatment alert before providing a treatment shock, and if the patient does not respond to the treatment alert (e.g., by holding down one or more response buttons), the device can deliver the treatment shock to restore normal heart rhythm.

Example Wearable Medical Device

FIG. 1 illustrates an example wearable medical device 100. The wearable medical device 100 includes a plurality of sensing electrodes 112 that can be disposed at various positions about the patient's body. The sensing electrodes 112 are electrically coupled to a medical device controller 120 through a connection pod 130. In some implementations, some of the components of the wearable medical device 100 are affixed to a garment 110 that can be worn on the patient's torso. For example, as shown in FIG. 1, the controller 120 can be mounted on a belt worn by the patient. The sensing electrodes 112 and connection pod 130 can be assembled or integrated into the garment 110 as shown. The sensing electrodes 112 are configured to monitor the cardiac function of the patient (e.g., by monitoring one or more cardiac signals of the patient). While FIG. 1 shows four sensing electrodes 112, additional sensing electrodes may be provided, and the plurality of sensing electrodes 112 may be disposed at various locations about the patient's body.

The wearable medical device 100 can also optionally include a plurality of therapy electrodes 114 that are electrically coupled to the medical device controller 120 through the connection pod 130. The therapy electrodes 114 are configured to deliver one or more therapeutic defibrillating shocks, pacing pulses, and/or TENS pulses to the body of the patient if it is determined that such treatment is warranted. The connection pod 130 may include electronic circuitry and one or more sensors (e.g., a motion sensor, an accelerometer, etc.) that are configured to monitor patient activity. In some implementations, the wearable medical device 100 may be a monitoring only device that omits the therapy delivery capabilities and associated components (e.g., the therapy electrodes 114). In some implementations, various treatment components may be packaged into various modules that can be attached or removed from the wearable medical device 100 as needed.

As shown in FIG. 1, the wearable medical device 100 may include a user interface pod 140 that is electrically coupled to, integrated in, and/or integrated with, the user interface of the medical device controller 120. The user interface pod 140 can be attached to the patient's clothing or to the garment 110, for example, via a clip (not shown) that is attached to a portion of the user interface pod 140. Alternatively, the user interface pod 140 may simply be held in a person's hand. For example, such a user interface pod 140 can be a smartwatch or a smartphone. In some examples, the user interface pod 140 may communicate wirelessly with the user interface of the medical device controller 120, for example, using a Bluetooth®, Wireless USB, ZigBee, Wireless Ethernet, GSM, or other type of communication interface.

The controller 120 may include response buttons and a touch screen that the patient can interact with in order to communicate with the medical device 100. The controller 120 also includes a speaker for communicating information to the patient and/or a bystander. In some examples, when the controller 120 determines that the patient is experiencing cardiac arrhythmia, the speaker can issue an audible alarm to alert the patient and bystanders to the patient's medical condition. In some examples, the controller 120 can instruct the patient to press and hold one or both of the response buttons on the medical device controller 120 to indicate that the patient is conscious, thereby instructing the medical device controller 120 to withhold the delivery of one or more therapeutic defibrillating shocks. If the patient does not respond to an instruction from the controller 120, the medical device 100 may determine that the patient is unconscious and proceed with the treatment sequence, culminating in the delivery of one or more defibrillating shocks to the body of the patient.

Figure 2A:
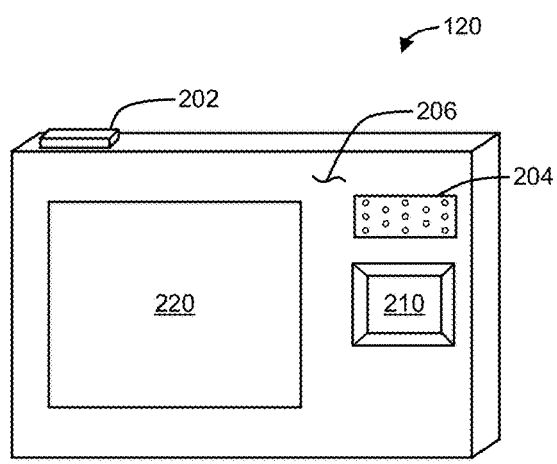
FIGS. 2A and 2B show an example medical device controller.
Figure 2B:
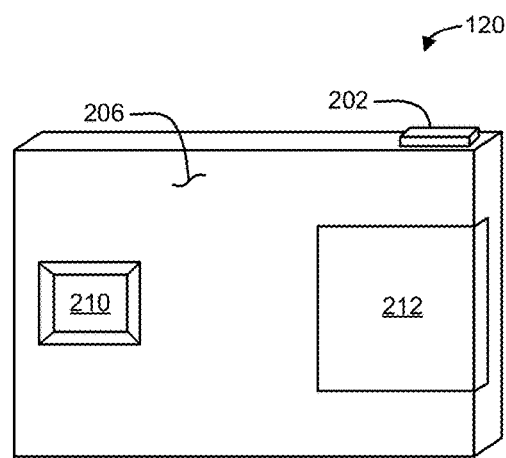

FIGS. 2A-2B show an example of the medical device controller 120. The controller 120 may be powered by a rechargeable battery 212. The rechargeable battery 212 may be removable from a housing 206 of the medical device controller 120 to enable a patient and/or caregiver to swap a depleted (or near depleted) battery 212 for a charged battery. The controller 120 includes a user interface such as a touch screen 220 that can provide information to the patient, caregiver, and/or bystanders. The patient and/or caregiver can interact with the touch screen 220 to control the medical device 100. The controller 120 also includes a speaker 204 for communicating information to the patient, caregiver, and/or the bystander. The controller 120 includes one or more response buttons 210. In some examples, when the controller 120 determines that the patient is experiencing cardiac arrhythmia, the speaker 204 can issue an audible alarm to alert the patient and bystanders to the patient's medical condition. In some examples, the controller 120 can instruct the patient to press and hold one or both of the response buttons 210 to indicate that the patient is conscious, thereby instructing the medical device controller 120 to withhold the delivery of therapeutic defibrillating shocks. If the patient does not respond to an instruction from the controller 120, the medical device 100 may determine that the patient is unconscious and proceed with the treatment sequence, culminating in the delivery of one or more defibrillating shocks to the body of the patient. The medical device controller 120 may further include a port 202 to removably connect sensing devices (e.g., ECG sensing electrodes 112) and/or therapeutic devices (e.g., therapy electrodes 114) to the medical device controller 120.

Figure 3:
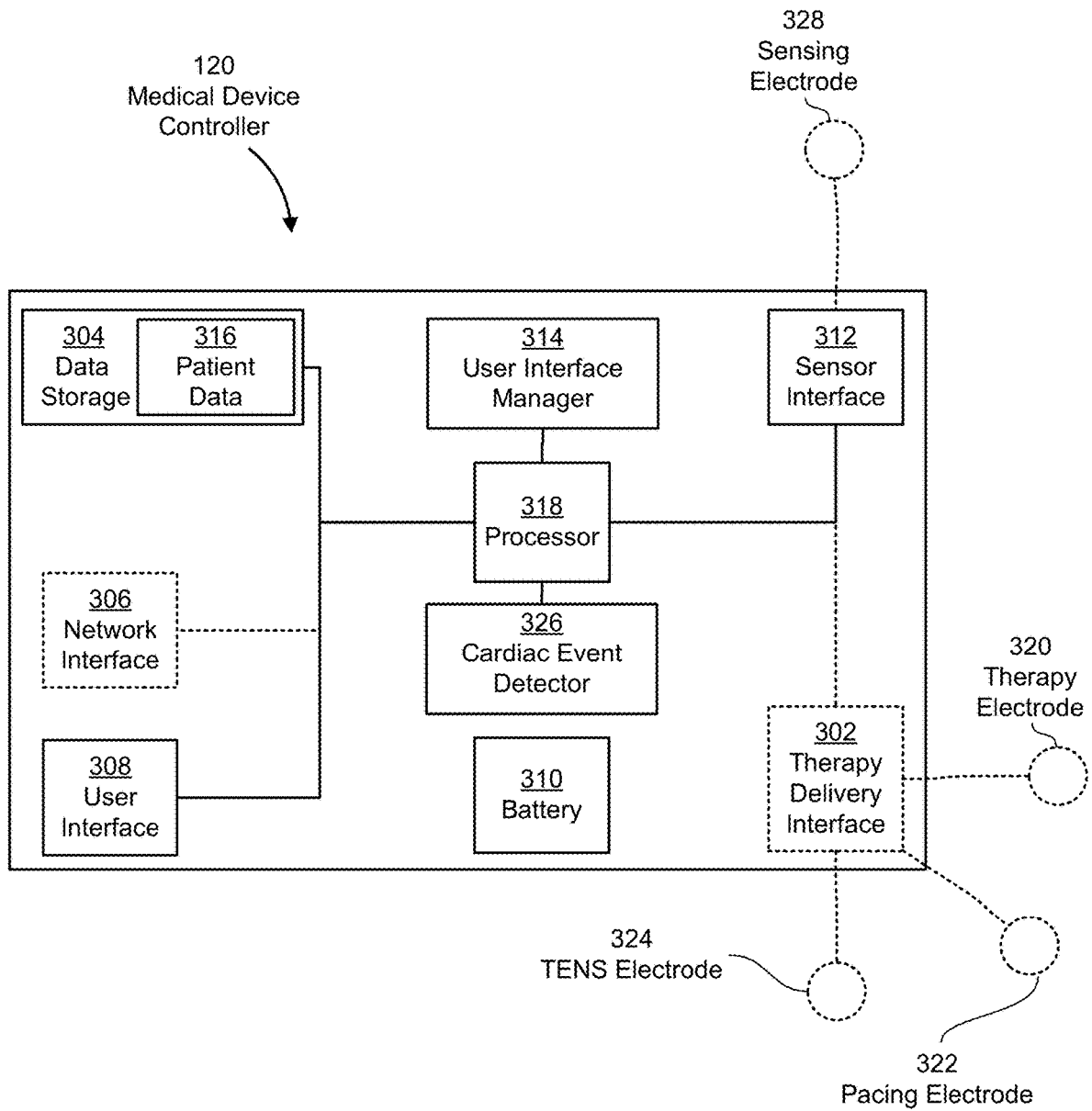
FIG. 3 shows a block diagram of an example medical device controller.

FIG. 3 shows a schematic of an example of the medical device controller 120 of FIGS. 1, 2A, and 2B. The controller 120 includes at least one processor 318, a user interface manager 314, a sensor interface 312, an optional therapy delivery interface 302, data storage 304 (which may include patient data storage 316), an optional network interface 306, a user interface 308 (e.g., including the touch screen 220 shown in FIG. 2), and a battery 310. The sensor interface 312 may be coupled to any one or combination of sensors to receive information indicative of cardiac activity. For example, the sensor interface 312 may be coupled to one or more sensing devices including, for example, sensing electrodes 328 configured to sense an electrocardiogram (ECG) signal of the patient. The therapy delivery interface 302 (if included) may be coupled to one or more electrodes that provide therapy to the patient including, for example, one or more therapy electrodes 320, pacing electrodes 322, and/or TENS electrodes 324. The sensor interface 312 and the therapy delivery interface 302 may implement a variety of coupling and communication techniques for facilitating the exchange of data between the sensors and/or therapy delivery devices and the controller 120.

In some examples, the network interface 306 can facilitate the communication of information between the controller 120 and one or more other devices or entities over a communications network. For example, the network interface 306 may be configured to communicate with a server (e.g., a remote server) where a caregiver can access information related to the patient. As discussed in more detail below with reference to FIG. 4, the network interface 306 may facilitate communication between the medical device controller 120 and a base station associated (e.g., paired) with the medical device controller.

In some examples, the medical device controller includes a cardiac event detector 326 to monitor the cardiac activity of the patient and identify cardiac events experienced by the patient based on received cardiac signals. In some examples, the cardiac event detector 326 can access patient templates (e.g., which may be stored in the data storage 304 as patient data 316) that can assist the cardiac event detector 326 in identifying cardiac events experienced by the particular patient.

The at least one processor 318 can perform a series of instructions that control the operation of the other components of the controller 120. In some examples, the user interface manager 314 is implemented as a software component that is stored in the data storage 304 and executed by the at least one processor 318 to control, for example, the user interface component 308. The user interface manager 314 may control various output components and/or devices of the medical device controller 120 to communicate with external entities consist with various acts and/or display screens described herein. For example, such output components and/or devices can include speakers, tactile and/or vibration output elements, visual indicators, monitors, displays, LCD screens, LEDs, Braille output elements, and the like.

In some implementations, the user interface component 308 can include one or more interfaces for communicating and/or interacting with different external entities. For example, such interfaces can include a caregiver interface for communicating and/or interacting with a caregiver (e.g., a nurse, a physician, a physician's aide or assistant, or other such individual or entity), a patient interface for a patient (or a layperson guardian of the patient), a patient service representative interface for a patient service representative, or a service interface for a service technician, among others. For example, the one or more interfaces can be displayed on a same physical display and/or touchscreen. In some cases, the external entities may be assigned separate security credentials that may be provided before access is granted to the corresponding interface. In some examples, the one or more interfaces can be displayed on different physical displays and/or touchscreens. For example, a caregiver interface may be displayed on a first display, and a patient interface may be displayed on a second, different display.

For example, the user interface manager 314 may cause the user interface component 308 to switch from a first one of the one or more interfaces to a second one of the one or more interfaces depending on a current device function or operation. As an example, the user interface component 308 may display "Call Caregiver" to the patient via a patient interface when a device related event is detected as described in further detail below. When the caregiver arrives, he or she may provide his or her security credentials and access a caregiver interface for addressing the device related event.

Example Monitoring Medical Device

In some examples, the medical device may be a patient monitoring device. For example, such a patient monitoring device may be configured to monitor one or more of a patient's physiological parameters without an accompanying treatment component. For example, a patient monitor may include a cardiac monitor for monitoring a patient's cardiac information. Such cardiac information can include, without limitation, heart rate, ECG data, heart sounds data from an acoustic sensor, and other cardiac data. In addition to cardiac monitoring, the patient monitor may perform monitoring of other relevant patient parameters, including glucose levels, blood oxygen levels, lung fluids, lung sounds, and blood pressure.

An example cardiac monitoring medical device (e.g., a cardiac monitor) may be similar to wearable medical device 100 described with reference to FIGS. 1-3 and omit, for example, the therapy electrodes 114 and/or the therapy delivery interface 302. In some implementations, the cardiac monitor is capable of and designed for being worn by a patient who is at risk of developing cardiac problems, but who does not yet meet criteria to be outfitted with a medical device that includes a treatment component (e.g., a defibrillator). Thus, the cardiac monitor may be prescribed so that continuous and/or event-based data can be sent from the cardiac monitor to a remote server. A caregiver can access the data from the remote server and determine whether the patient is experiencing or has experienced a cardiac problem. In some implementations, after determining that the patient is experiencing a cardiac problem, the caregiver may instruct the patient to begin wearing a medical device with treatment capabilities.

In some implementations, the patient can interact with the user interface 308 to identify a patient symptom. The user interface 308 may include a drop down menu or check list that allows the patient to select a particular symptom from a list of alternatives. Options for patient systems can include one or more of: feeling a skipped beat, shortness of breath, light headedness, racing heart rate, fatigue, fainting, chest discomfort, weakness, dizziness, and/or giddiness. In addition, the patient can select a level of activity (e.g., light activity, moderate activity, rigorous activity, etc.) that he or she was performing when the symptom occurred. In some implementations, in response to the selection by the patient, the cardiac event detector 326 can cause a portion of patient physiological information (e.g., in the form of a cardiac signal) to be captured for a length of time that is based on when the symptom was experienced. For example, the cardiac event detector 326 can cause a portion of an ECG signal of the patient to be captured. The portion of the ECG signal is sometimes referred to herein as an ECG strip. In some implementations, the cardiac monitor can continuously record ECG data, and at the same time also identify and record one or more ECG strips relating to one or more events of interest (e.g., patient-reported symptoms, events detected by the cardiac event detector 326, etc.). As such, if a caregiver wishes to view ECG data for a period of time prior to or after the recorded ECG strip relating to an event of interest, such data is available for review from the continuously-recorded ECG data.

Example Base Station

Figure 4:
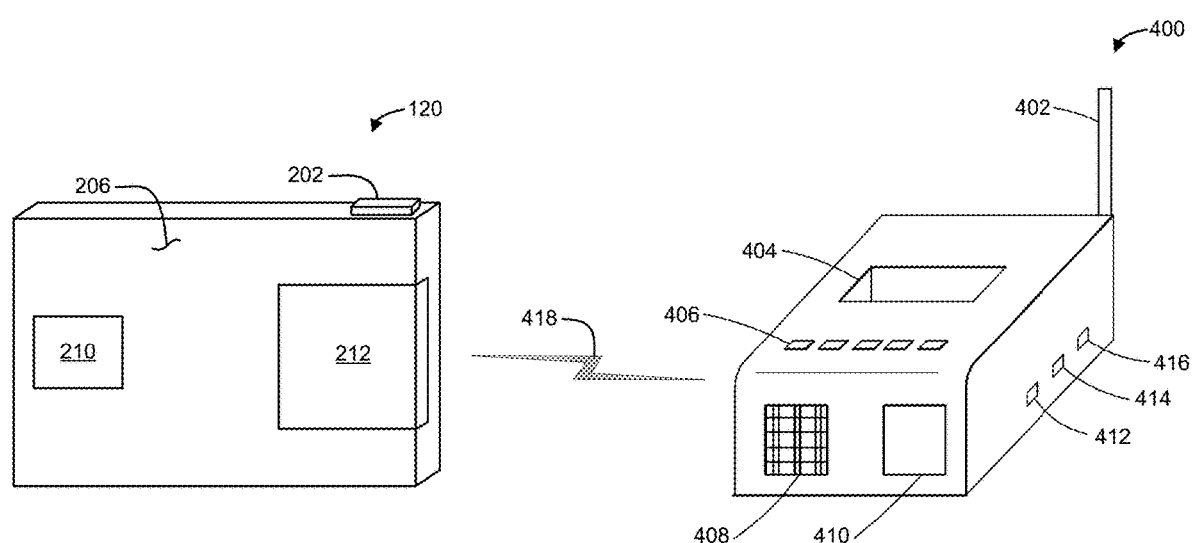
FIG. 4 shows an example medical device controller in communication with an example base station.

In some examples, the medical device controller may be in communication with a base station capable of performing a number of different functions. FIG. 4 illustrates an example medical device controller 120 in communication with a base station 400. As illustrated, base station 400 includes an antenna 402, a battery charging bay 404, one or more buttons 406, a speaker 408, a display 410, and one or more communication interfaces 412, 414, and 416. It is appreciated that the base station 400, in some examples, may omit one or more of the elements depicted in FIG. 4.

The base station 400 communicates with the medical device controller via, for example, wired or wireless communication link 418. With respect to wireless communication, such a link 418 may be implemented through any one or combination of wireless communication standards and protocols including, for example, BLUETOOTH, Wireless USB, ZigBee, and Wireless Ethernet. In some examples, the medical device controller 120 may be paired to (e.g., connected to) a particular base station 400 through one or more procedures as described further below. The medical device controller 120 may provide, for example, information regarding the patient's medical condition and/or the status of the medical device to the base station 400.

The information received by the base station 400 may be communicated over a wired or wireless network shortly after it is received by the base station 400, or alternatively, may be stored in a memory of the base station 400 and communicated over the network at a later time. For example, the network can be a telephone or cellular service network (e.g., Global System for Mobile Communications (GSM), High Speed Packet Access, mobile network standards known as 3G, 4G, Long Term Evolution (LTE), or LTE Advanced, or the like. For example, the network can be a wired computer network that connects the base station 400 to a local area network (LAN), wide area network (WAN), the Internet, or the like. To facilitate wired network connections, the base station 400 can include one or more ports (e.g., RJ-45, or telephone cable ports) as further described below. The information that is communicated by the base station 400 may be retained in the memory of the base station 400.

Another of the functions performed by the base station 400 is to store and/or communicate information received from the medical device controller 120 over the wired or wireless communication network. For example, information relating to the device and/or patient's medical condition over a period of time may be communicated periodically or aperiodically by the base station 400 to a remote location. For example, the remote location can include equipment for securely receiving such medical data over the network. For example, the remote location may be a technical service center for receiving and processing the information from the base station 400. In some examples, the information may be complied into a report and provided to a medical care provider, e.g., the patient's doctor in a report. Such reports may be configured to be provided periodically, such as daily, weekly, or monthly, or in response to a user, device, or doctor triggered event.

For example, the remote location may be a medical service provider, such as a doctor, so that the doctor may remotely monitor the patient's medical condition. The base station 400 also includes several different communication interfaces including: a device communication interface 412 to receive information from the controller 120 of the medical device controller 120, a telephone network interface 414 to communicate, via a telephone network, the information received from the medical device controller 120, and a network interface 416 to communicate, via a wired network connection, the information received from the medical device controller 120. In certain embodiments, the base station 400 also includes an antenna 402 that can wirelessly communicate the information received from the medical device controller 120 via a cellular (e.g., 2G, 3G, and 4G) network.

In some examples, the base station 400 is capable of charging a rechargeable battery for the medical device controller 120. In these examples, the base station 400 may include a battery charging bay 404 constructed to receive and charge a battery for the medical device controller (e.g., battery 212). The medical device may be provided with multiple batteries to enable a patient and/or caregiver to charge one battery while another charged battery is used to provide power to the medical device. The batteries may be swapped between the medical device controller 120 and the base station 400 once the battery in the medical device controller is depleted (or near depleted). It is appreciated that the base station 400 may include any number of battery charging bays 404 to, for example, charge multiple batteries for the medical device controller 120 simultaneously.

Example Medical Device for Use in a Health Care Facility Setting

As discussed above, the medical device controller 120 may be well-suited for a range of different cardiac monitoring and/or treatment devices. In some examples, the medical device controller 120 is part of a medical device for use in an inpatient context, e.g., for use with patients admitted to a health care facility, such as, a hospital. In an example, when a patient is admitted to a health care facility, such as a hospital, medical devices as described herein can be configured for continuous, substantially continuous, long-term and/or extended use or wear by, or attachment or connection, to the patient. For example, the patient can be cared for in the health care facility for a period ranging from a few minutes or hours of observation and/or treatment, to days, weeks, or even months. In operation, such a hospital based medical device may operate in a manner such that an interface, prompts, and communication performed by the hospital based medical device can be configured for and/or directed to a user other than the patient 102, e.g., a caregiver such as a nurse or a patient service representative in the health care facility. For example, a caregiver can program the device and/or set the medical device up for use by the patient 102 admitted to the health care facility. The interface, prompts, and communication can be directed to the patient 102 in scenarios such as when a response is required to let the device know whether or not the patient 102 is conscious, which can be used in deciding when to shock the patient 102, and when a patient is given an alert to call the caregiver (e.g., "Call Caregiver" as described in further detail below).

Figure 5:
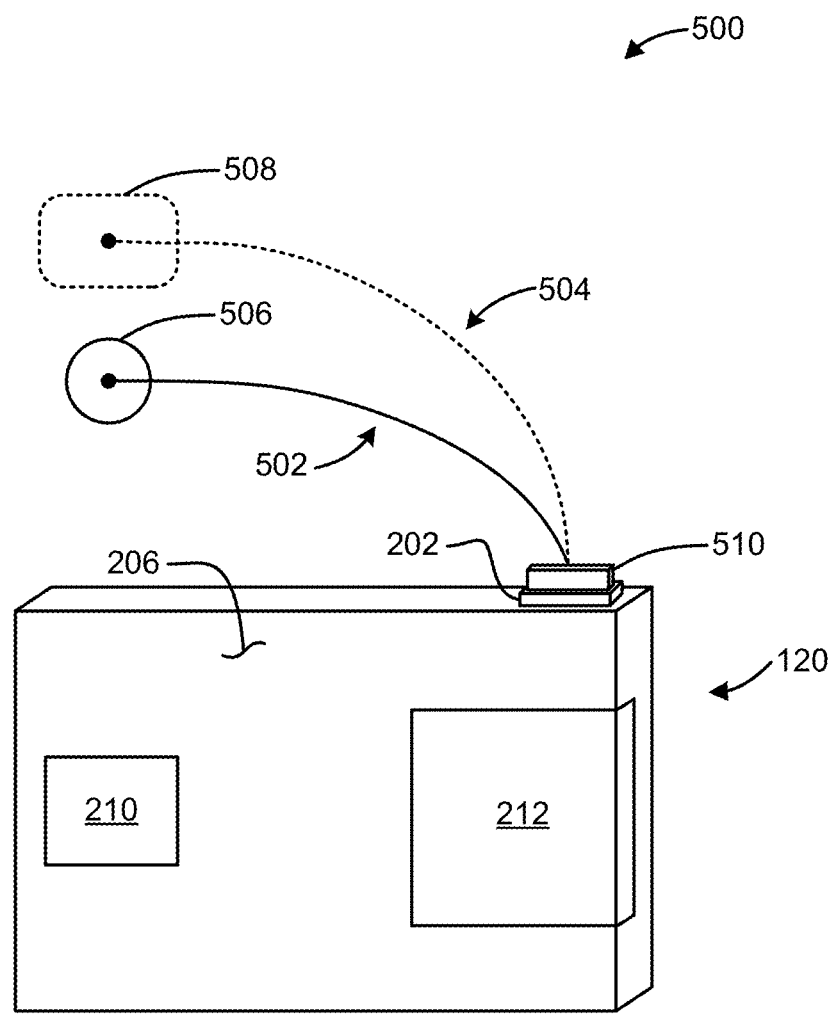
FIG. 5 shows an example medical device for monitoring and treatment patients in a healthcare facility.

FIG. 5 illustrates an example hospital based medical device employing the medical device controller 120. The hospital based medical device may be constructed to provide cardiac monitoring and/or treatment for patients in a hospital setting who may be, for example, bedridden and/or limited-mobility patients. For example, such patients' movement may be limited to a room within or a portion of the health care facility for at least a substantial portion of the time that the patient is admitted to the health care facility. Providing such patients in with the hospital based medical device may, in some cases, advantageously reduce the time between the patient experiencing a cardiac event and the notification of hospital staff, the administration of life-saving defibrillation pulses, and/or the administration of pacing pulses. For example, hospital patients who may experience a cardiac event might have to wait for a physician to go to the patient's room, assess the condition of the patient, locate a defibrillation device, attach the defibrillation device to the patient, and provide treatment to the patient. The hospital based medical device as described herein can provide continuous, substantially continuous, long-term and/or extended monitoring of a patient for cardiac arrhythmias or other physiological conditions and, in response to detecting a treatable condition, provide a treatment to the patient (e.g., one or more pulses or shocks to convert a cardiac arrhythmia). For example, reducing the time between the patient experiencing a life-threatening cardiac event and providing life-saving defibrillation or pacing pulses can improve the likelihood of the patient surviving the cardiac event.

As illustrated in FIG. 5, the hospital based medical device 500 includes the medical device controller 120 and a sensing component 502. The sensing component 502 includes a connector 510 constructed to removably couple to the port 202 of the medical device controller 120. The sensing component 502 may detect information indicative of cardiac activity of the patient including, for example, ECG activity, tissue fluid, lung fluid, lung sounds, heart sounds, and/or patient activity. In some examples, the sensing component 502 includes one or more electrodes 506. The electrodes 506 may be stick-on adhesive electrodes constructed to attach to the patient. In some examples, the electrodes 506 may be detachable from a wire lead coupling the electrode 506 to the connector 510. Constructing the sensing component 502 to make the electrodes 506 detachable may enable the patient and/or caregiver to periodically (e.g., every 24-48 hours or more, as prescribed) replace the electrodes 506 without replacing the entire sensing component 502. For example, the electrodes 506 may be long term wear electrodes that are configured to be continuously worn by a patient for extended periods (e.g., 3 or more days). One example of such an electrode is described in U.S. Patent Application Publication No. US2013/0325096, titled "LONG TERM WEAR MULTIFUNCTION BIOMEDICAL ELECTRODE," (hereinafter the "'096 publication") published Dec. 5, 2013 and issued as U.S. Pat. No. 9,737,701.

In some examples, the hospital based medical device 500 may also include a treatment component 504 to provide treatment to the patient. The treatment component 504 may include, for example, a therapy pad 508 configured to attach to the patient. The treatment component 504 may be connected to the same connector 510 as the sensing component 502 and/or employ a separate connector that is capable of coupling to the connector 510 in a modular fashion. It is appreciated that the treatment component 504 may be integrated into the sensing component 502 in a combined sensing-treatment component. The combined sensing-treatment component may include an electrode with integrated sensing and treatment delivery capabilities as described in the '096 publication. Although one therapy pad 508 is depicted for illustration purposes, it should be appreciated that more than one therapy pad 508 may be provided.

In some examples, the controller 120 of the hospital based medical device 500 is communicatively coupled to a base station such as base station 400 described above. The hospital based medical device 500 may communicate, for example, patient information and/or status information of the medical device to the base station 400. In these examples, the base station 400 may issue alerts to medical personnel (e.g., at the hospital) and/or provide the information to a remote server that is accessible by medical personnel.

New Patient Setup

Figure 6A:
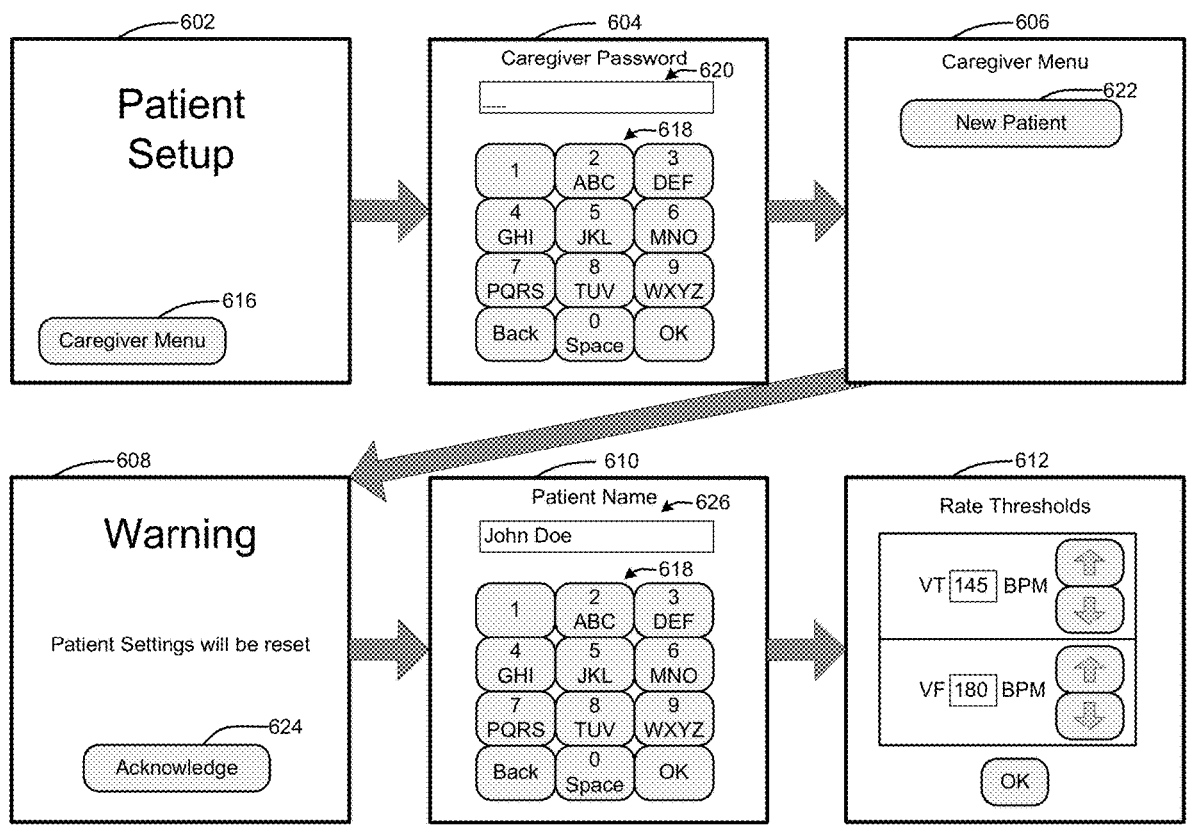
FIGS. 6A and 6B show an example set of screens for patient setup on a medical device.
Figure 6B:
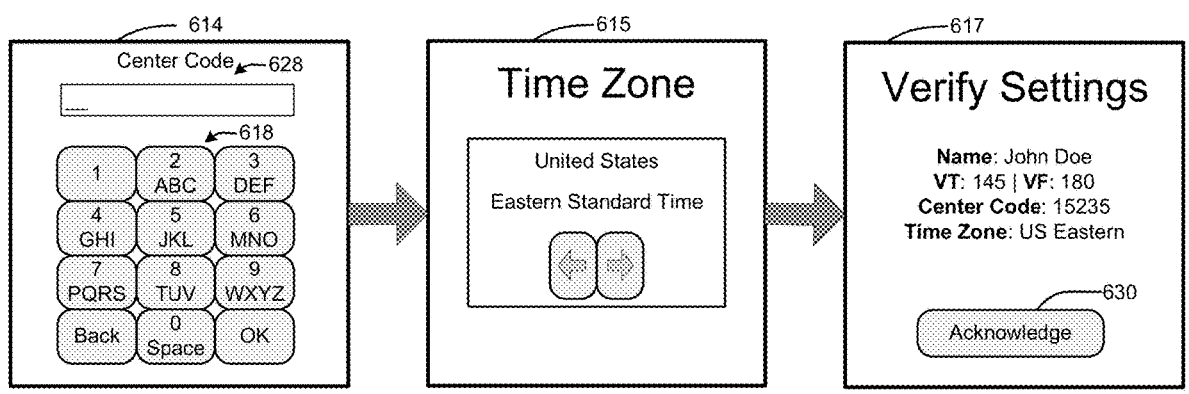

In some examples, a caregiver (e.g., a nurse, a physician's aide or assistant, or a physician) may configure the medical device for the patient in the health care facility prior to deploying the device on the patient. For example, the caregiver may access the setup screen via a caregiver interface to initiate a device-guided patient setup process. In the following description, although the user interacting with the medical device is described as being a caregiver, it is appreciated that the user can be any authorized person involved in the care or treatment of the patient or the deployment of the medical device, e.g., a patient service representative). For example, a patient service representative may access the device-guided patient setup via a separate patient service representative interface. For example, the caregiver may input patient information into the medical device in order to adapt the device to the patient. FIGS. 6A and 6B illustrate an example set of user interface screens displayed to the caregiver via, for example, touch screen 220 on the medical device controller 120 to setup the medical device. It is further appreciated that the screens and screen sequences described below are for illustration only and should not be construed as being the only way to implement the concepts described herein. For example, in the context of new patient setup, the sequence of caregiver screens or the screens themselves can be changed from those shown in FIG. 6A or 6B to include other screen sequences or screens related to device and/or patient setup without departing from the spirit of the concepts described herein.

For example, the medical device controller 120 may be configured to display the set of user interface screens to the caregiver illustrated in FIGS. 6A and 6B responsive to the device either being manually placed in (e.g., through a user providing input) or automatically entering a new patient mode. The new patient mode may be invoked by, for example, fitting the medical device to a new patient. The medical device may detect that a new patient is being fitted by, for example, monitoring a status of the port 202 of the medical device controller 120. For example, the medical device may enter the new patient mode responsive to one or more devices (e.g., cardiac sensing component 502) being disconnected from the port 202, one or more devices being connected to the port 202, and/or a battery being connected to the medical device. In some examples, the device may, through the sensing component 502, detect that the patient's ECG profile is significantly different from one or more baseline ECG profiles stored in the device's memory. In such cases, the device can automatically enter the new patient mode.

In some examples, where a same patient that was previously using the device is being reconnected to the device, the caregiver can cause the device to exit the new patient mode and continue using the patient's previously entered information. In some examples, the caregiver may be prompted to review the patient's information and confirm the same.

As shown in screen 602, the medical device controller may display a caregiver menu button 616 that allows a caregiver to access the caregiver interface. For example, the medical device controller may proceed to screen 604 upon detection of the menu button 616 being activated (e.g., tapped by a caregiver). In screen 604, the medical device controller requests a caregiver password to be entered into the password field 620 via a keypad 618 prior to granting access to the caregiver interface. The medical device controller may request security credentials to limit access to the new patient setup to certain individuals involved in providing care to the patient. For example, the medical device controller may restrict access to the new patient setup to a caregiver (e.g., a nurse) who has been previously authorized access to the caregiver interface. In some examples, the device can be configured to provide different access levels to personnel involved in the patient's care along with corresponding different sets of security credentials. For example, a physician, physician's aide or assistant, nurse, a designee, or other authorized person may have separate sets of credentials, and their corresponding profiles and access levels may allow them to modify the device's settings with respect to the patient treatment protocol (e.g., rate thresholds and/or energy levels of each treatment shock). In one implementation, the device can be set up such that only a user with physician level access can modify the patient treatment protocol. In another implementation, the device may be set up to allow a user with caregiver level access, e.g., any of a physician, physician's aide or assistant, nurse, a designee, or other authorized person, to modify the patient treatment protocol. Hospital administrative personnel, on the other hand, may be limited to entering the patient information (e.g., patient's name, age, and such information) and may not be able to modify the treatment parameters without prior explicit authorization. In various implementations, an authorized technical service representative may be able to access additional device settings not available to any of the other users of the device. In some examples, the patient may be permitted to access (e.g., with or without security credentials) a limited set of options via the user interface.

If the medical device controller determines that the password entered via the keypad matches the password for the device (e.g., a password stored in the memory or at a remote database securely accessible by the device), the medical device controller proceeds to screen 606 of the caregiver interface.

In screen 606 of the caregiver interface, the medical device controller displays a caregiver menu including one or more options. As noted, depending on the user profile (physician or patient service representative), the menu may provide different options corresponding to the allowed interactions permitted for the user. In this case, for example, the caregiver options may include, for example, a new patient option as illustrated by the new patient button 622. The medical device controller proceeds to screen 608 responsive to the new patient button 622 being activated where a warning is presented to the caregiver that can be acknowledged by the acknowledge button 624. In screen 610 the patient's name may be entered in the patient name field 626 via the keypad 618. In screen 612, heart rate thresholds for ventricular tachycardia (VT) and ventricular fibrillation (VF) may be received from the caregiver. The medical device controller proceeds to screen 614 illustrated in FIG. 6B once the VT and VF thresholds are received from the caregiver.

In screen 614, the medical device controller receives a center code associated with the facility where the medical device is deployed in the center code field 628 via the keypad 618. The medical device controller receives information regarding the current time zone in screen 615 and displays the settings received from the caregiver in screen 617 that can be acknowledged by the acknowledge button 630.

Configuration of the Medical Device

The medical device controller, in some implementations, may allow a caregiver to configure the medical device controller after the initial setup described above with respect to FIGS. 6A and 6B. For example, the medical device controller may allow a caregiver to pair the medical device controller with a particular base station.

As noted, in a busy hospital environment, there may be a plurality of base stations within vicinity of the medical device controller. As such, it may be necessary for the controller to be configured to be paired with a particular base station to be associated with the patient using the medical device. When a patient is discharged and the device reconfigured to be used with a new patient, it may be necessary to re-pair the device with a same or a different base station depending on which base station is being used for the new patient. Moreover, a caregiver may wish to check in on the patient to view a status of the device to ensure that the device is operating well and that no exceptions have been reported. A caregiver may wish, for example, to check on a status of the electrodes, confirm that the ECG data is being correctly received, monitored, and stored, or, in the event of a patient symptom, record an ECG strip for subsequent analysis.

Various status parameters of the medical device controller may also be made accessible to the caregiver to enable the caregiver to, for example, troubleshoot the medical device and/or assess a medical condition of the patient. FIGS. 7A-7D illustrate an example set of caregiver interface screens displayed by the medical device controller to enable a caregiver to pair the medical device with a base station (FIG. 7A), monitor the electrode status (FIG. 7B), see live ECG data (FIG. 7C), and record the heart rhythm of the patient (FIG. 7D).

Figure 7A:
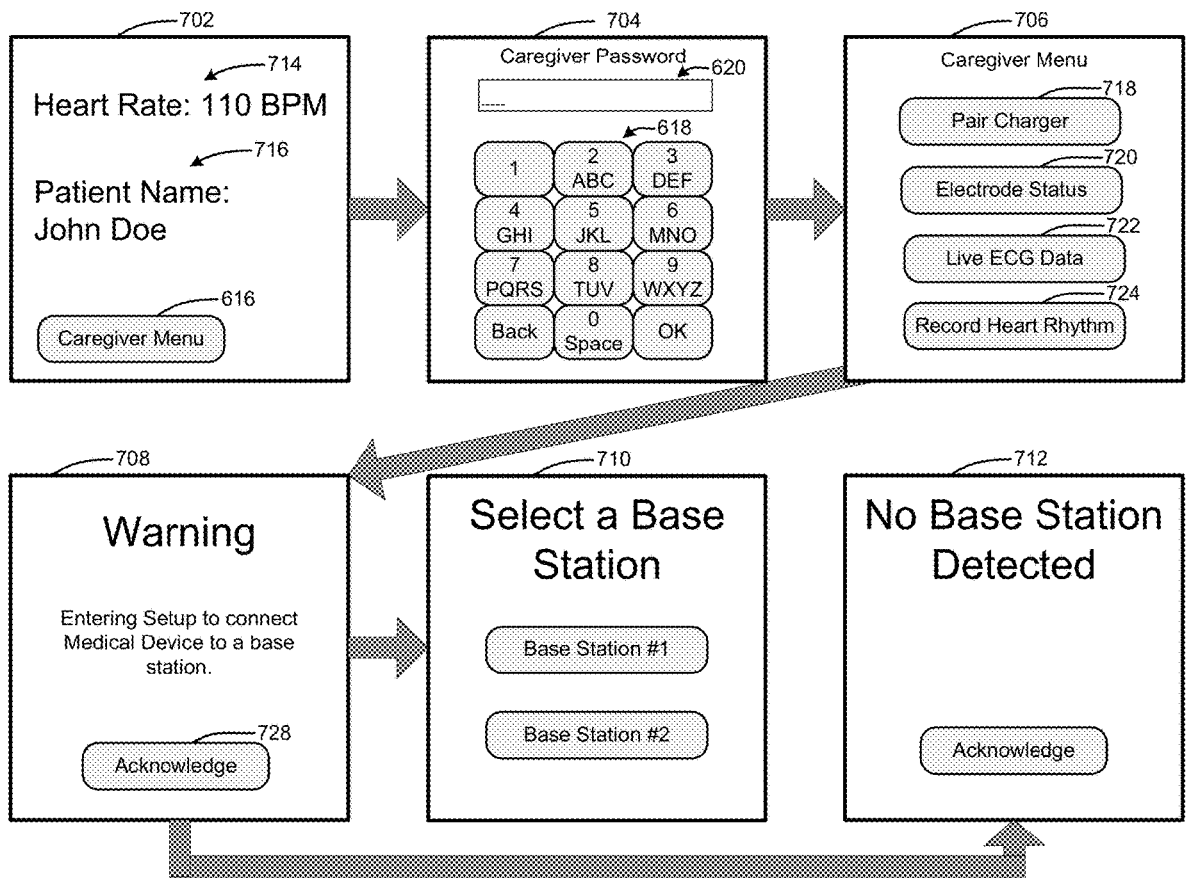
FIGS. 7A-7D show an example set of screens for configuring and operating a medical device.

Referring to FIG. 7A, a home screen is displayed to the caregiver in screen 702 including, for example, the heart rate of the patient 714, the name of the patient 716, and a caregiver menu button 616. As described above with respect to FIG. 6A, the medical device controller may present the caregiver menu screen 706 of the caregiver interface after receiving the correct caregiver password in screen 704. The caregiver menu screen 706 includes one or more options including a pair charger button 718, an electrode status button 720, a live ECG data button 722, and a record heart rhythm button 724. The medical device controller proceeds to screen 708 responsive to activation of the pair charger button 718 in screen 706 and displays a warning that may be acknowledged by the acknowledge button 728. The medical device controller proceeds to screen 710 and displays the nearby base stations that may be selected by the caregiver. If no base stations are detected, the medical device controller displays screen 712 informing the caregiver that no base stations were detected.

Figure 7B:
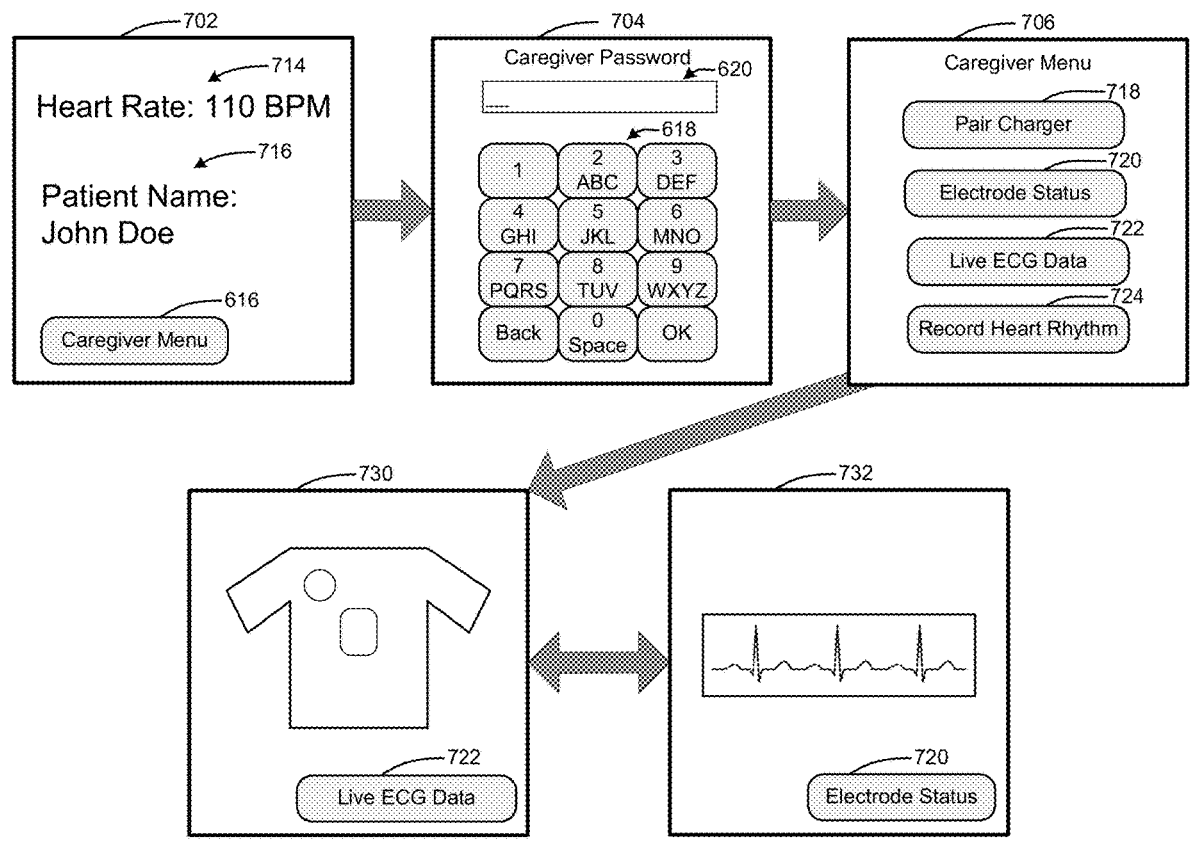
Figure 7C:
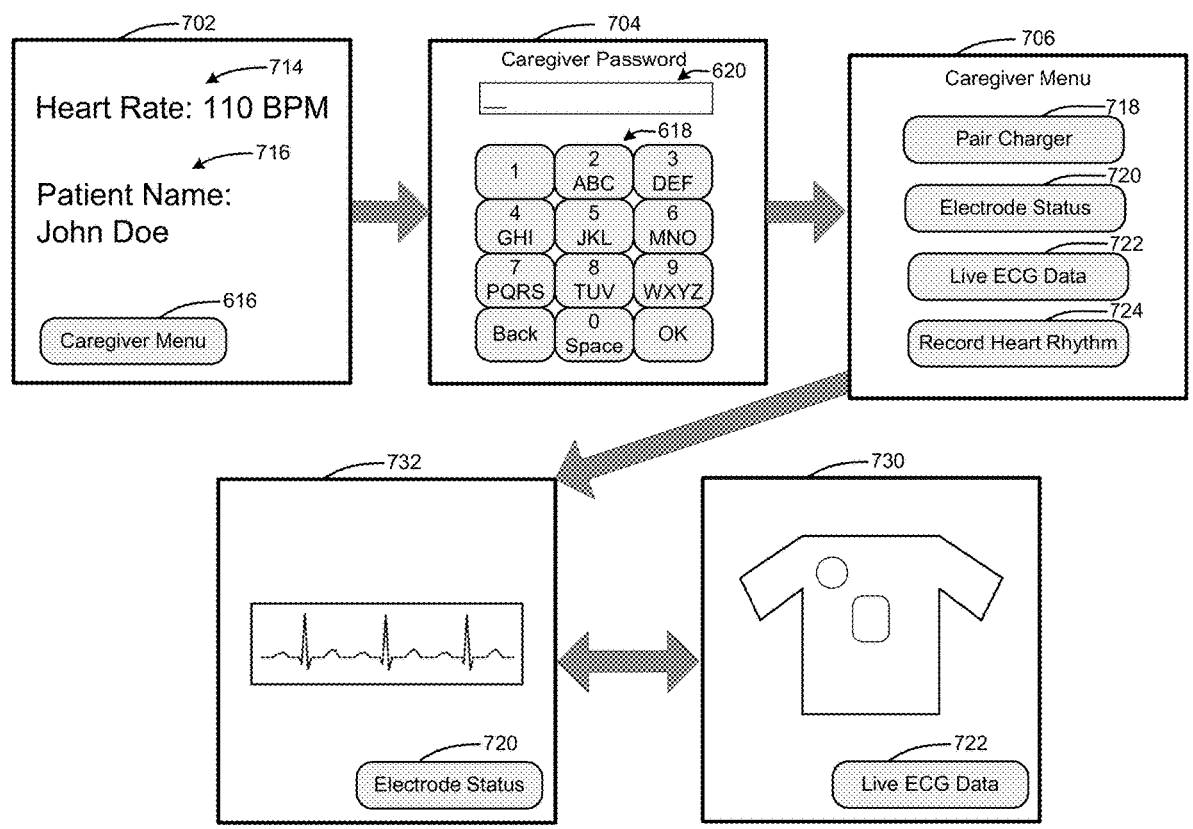
Figure 7D:
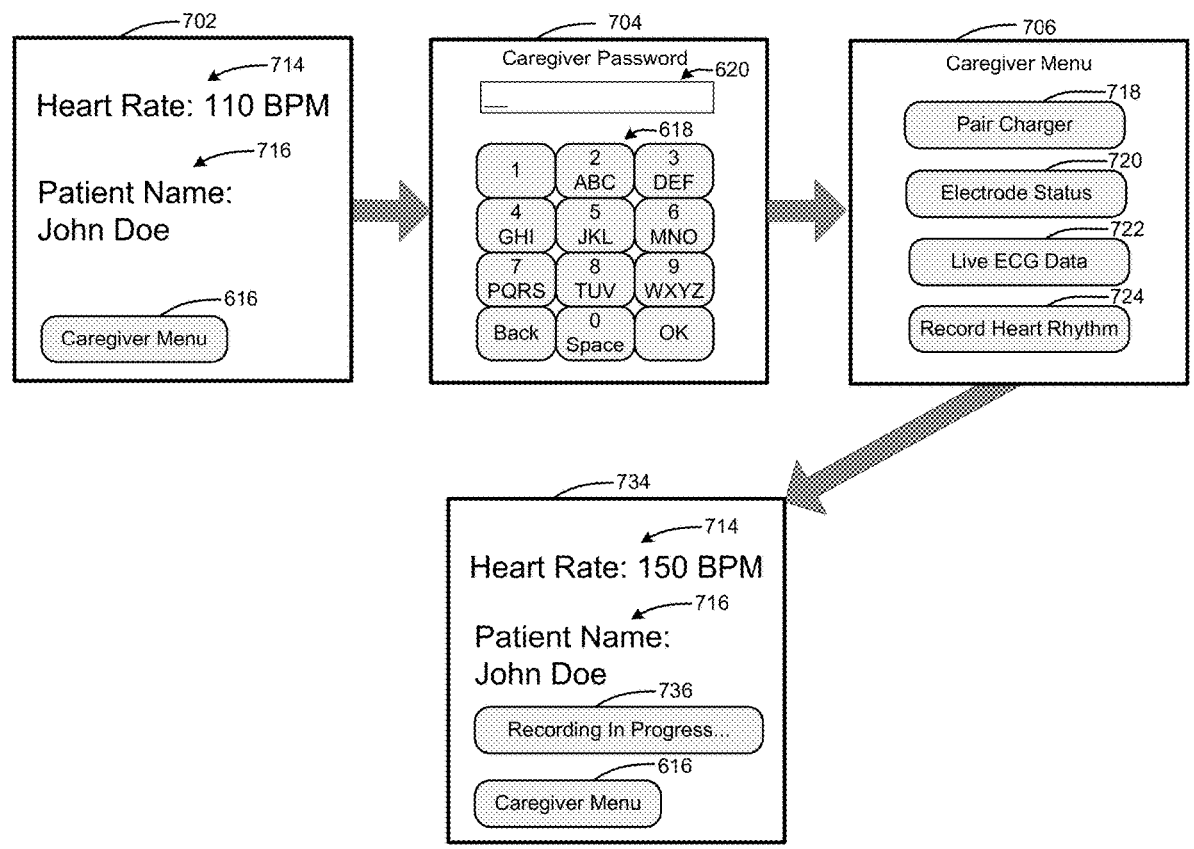

FIG. 7B illustrates the same first three screens 702, 704, and 706 as described above. The medical device proceeds to screen 730 responsive to the electrode status button 720 being activated in screen 706 illustrating the status of the one or more electrodes (e.g., sensing or treatment) attached to the patient. The screen 730 may show a checkmark on electrodes that are properly attached to the patient and an "X" mark on electrodes that are improperly attached to the patient to indicate to the caregiver which electrodes need attention. The medical device may also display the live ECG data button 722 in screen 730 to enable a caregiver to cause the medical device to transition to screen 732 showing live ECG data of the patient. FIG. 7C illustrates a similar set of screens 702, 704, 706, 730, and 732 in a different sequence caused by activation of the live ECG data button 722 in screen 706 (as opposed to the electrode status button 720).

FIG. 7D illustrates the same first three screens 702, 704, and 706 as described above. The medical device proceeds to screen 734 responsive to the record heart rhythm button 724 being activated. Screen 734 adds a recording in progress indicator 736 to the home screen 702. The recording in progress indicator 736 provides a notification to the caregiver that the ECG signal of the patient is being recorded by the medical device. The medical device may also transmit the recorded ECG data to a remove server (e.g., via a base station) for later access by various medical personnel.

Figure 8A:
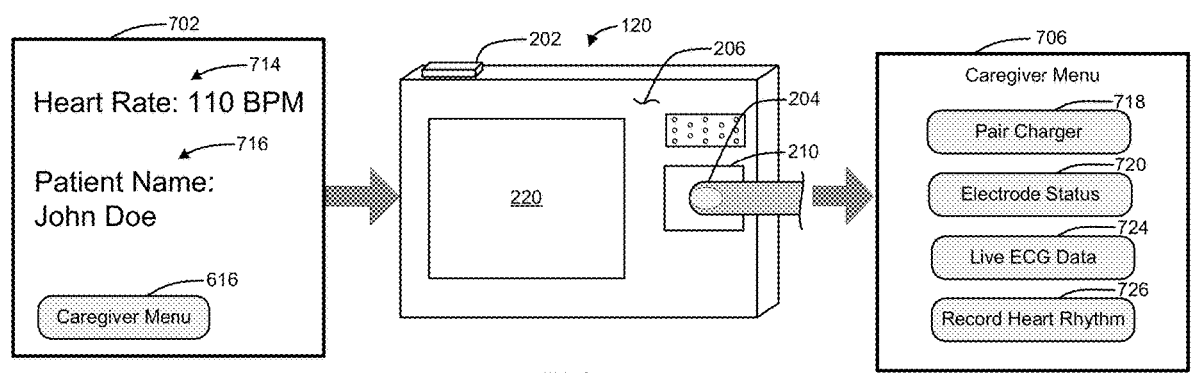
FIGS. 8A and 8B show example procedures for accessing various caregiver information.
Figure 8B:
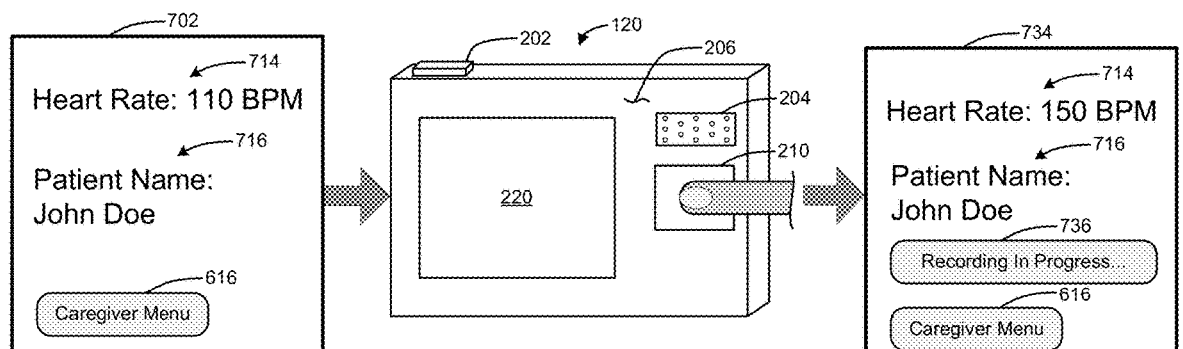

It is appreciated that other mechanisms apart from the password and keypad illustrated in screens 604 and 704 may be employed as security credentials by the medical device to limit access to one or more screens in the caregiver interface. For example, the medical device may employ a unique series of interactions with the medical device. As illustrated in FIG. 8A, the caregiver menu screen 706 may be accessible after the medical device receives a unique set of pushes (e.g., three pushes in sequence) of the response button 210. In some examples, the unique sequence of events may be employed to invoke one or more specific actions to be performed by the medical device and, thereby, bypass the caregiver menu illustrated in screens 606 and/or 706. For example, as illustrated in FIG. 8B, the medical device may automatically begin recording the ECG signal of the patient and transition to screen 734 responsive to detecting a unique series of pushes of the response button 210.

It is appreciated that yet other mechanisms may be employed to limit access to various screens of the user interface. For example, the medical device may include voice recognition capability and the medical device may display the caregiver menu in screen 606 responsive to receiving a voice command from a caregiver that matches a stored voice signature.

Training the Patient

Figure 9A:
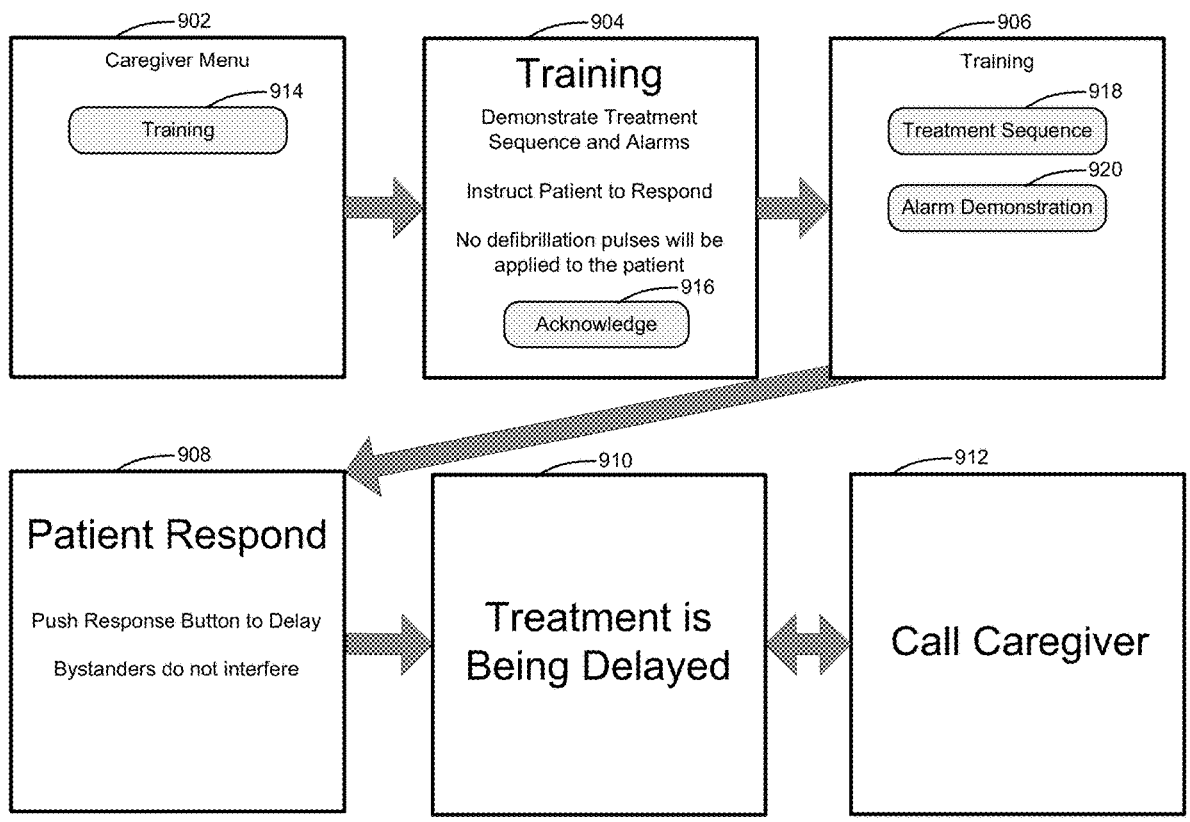
FIGS. 9A-9C show an example set of screens for a caregiver to administer training to a patient.
Figure 9B:
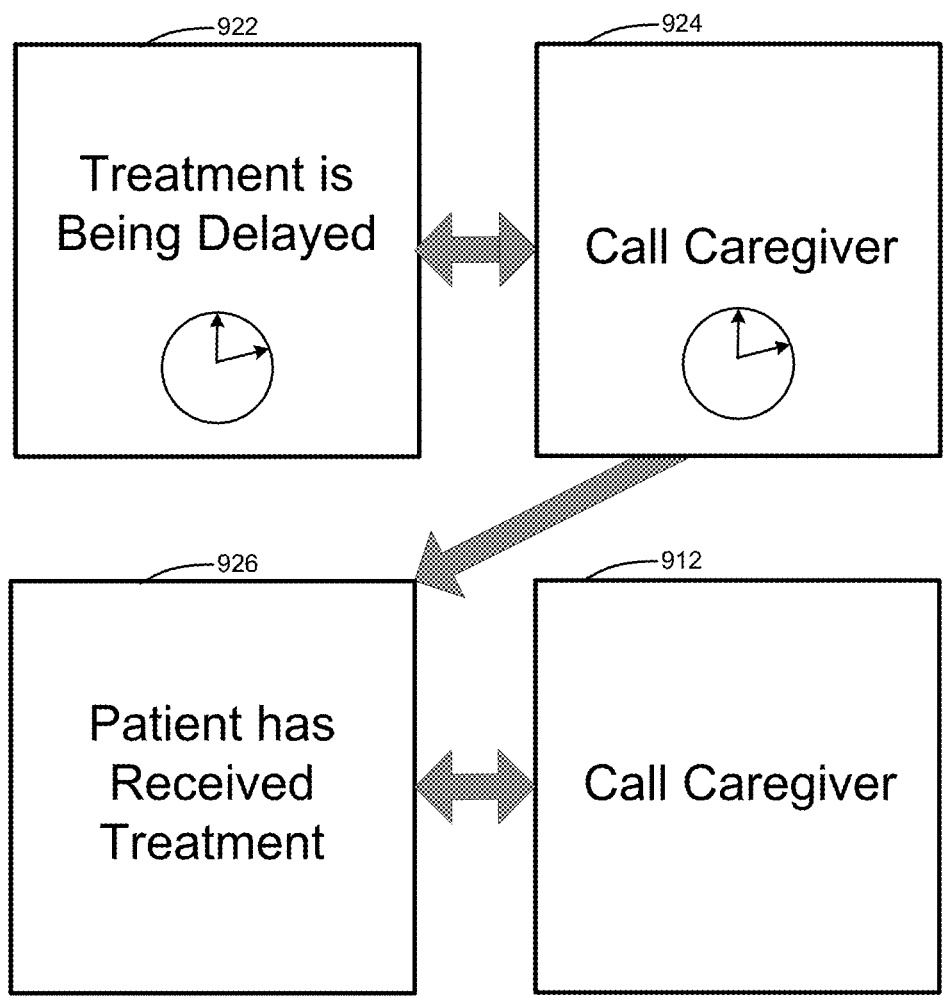
Figure 9C:
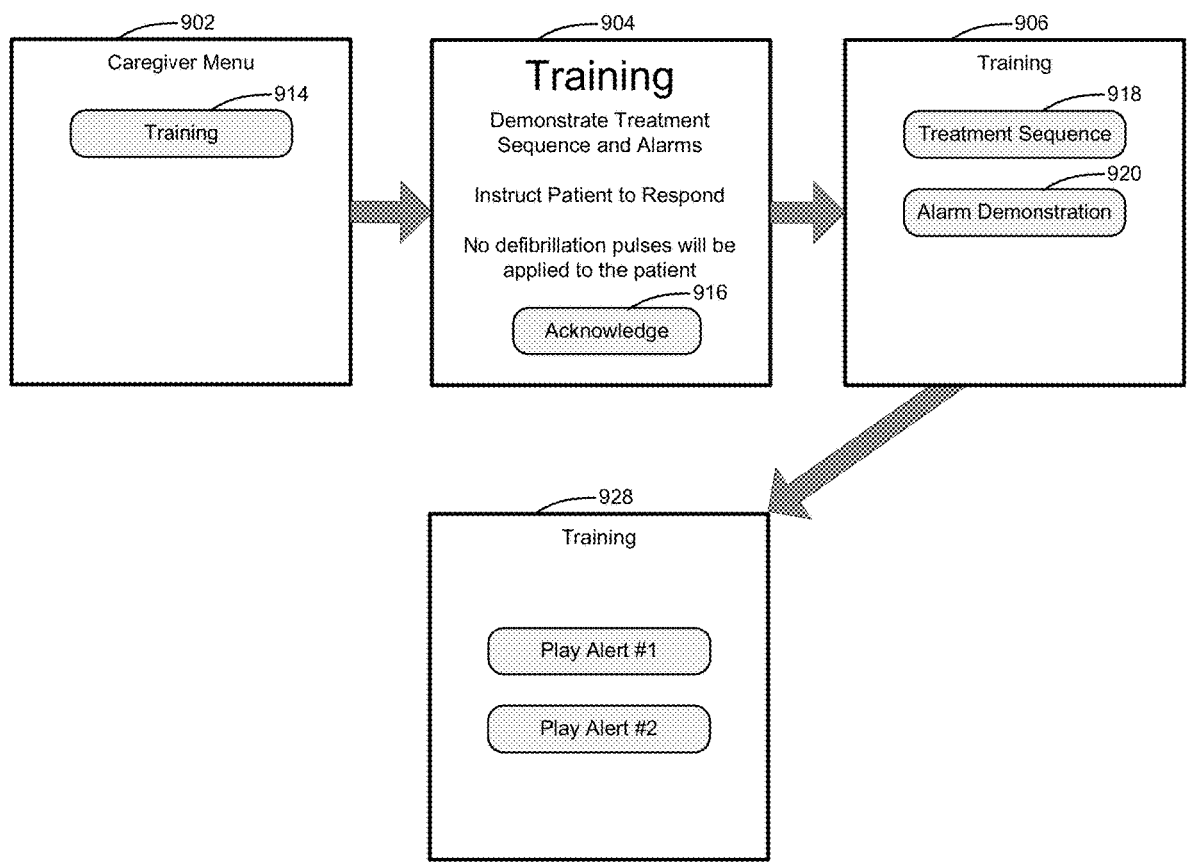

The medical device may provide the caregiver access to one or more training modules for the caregiver to administer to the patient. The patient may be unfamiliar with the medical device and/or incorrectly assume that he or she should not touch or interact with the medical device regardless of the circumstances. These training modules may be administered the patient to familiarize the patient with the medical device. FIGS. 9A-9C illustrate an example set of caregiver interface screens for the caregiver to administer training to the patient. It is appreciated that the screens illustrated in FIGS. 9A-9C may be preceded by one or more screens requiring security credentials of the caregiver including, for example, screens 702 and 704 illustrated above in FIGS. 7A-7D.

Referring to screen 902 in FIG. 9A, an example caregiver menu is shown including a training button 914 that causes the medical device to transition to screen 904 responsive to being activated. The screen 904 provides a reminder to the caregiver to demonstrate the treatment sequence to the patient and/or remind the caregiver to reassure the patient that no defibrillation pulse will be provided to the patient during the training. The medical device may transition to screen 906 once the acknowledge button has been activated. Screen 906 illustrates a training screen with various training modules to select including, for example, a treatment sequence demonstration module (activated by button 918) and an alarm demonstration module (activated by button 920). The medical device transitions to screen 908 responsive to the treatment sequence button 918 being activated. Screen 908 provides a notification to the patient to respond by pushing the response button and/or informs bystanders not to interfere with the treatment sequence. The medical device transitions to screen 910 responsive to the response button 210 being pushed. Screen 910 indicates that the treatment is being delayed and alternates with screen 912 informing the patient to call the nurse or other caregiver.

The medical device transitions to caregiver interface screen 922 in FIG. 9B once the response button 210 has been released where a notification that the treatment is being delayed is displayed in combination with a timer counting down until treatment is provided to the patient. The screen 922 alternates with the call caregiver screen 924 that may also include the timer counting down until the administration of treatment. The medical device transitions to screen 926 once the timer has expired without administering therapy (because the medical device is in a training mode) notifying the patient that treatment has been administered. The screen 926 may alternate with the screen 912 notifying the patient to call the nurse or other caregiver. Were the medical device not in a training mode, treatment would be provided to the patient and the medical device may alternate between display screen 926 and 912 as shown.

In FIG. 9C, the first three screens 902, 904, and 906 may be similar to the screens described above with the same reference numbers. FIG. 9C illustrates that sequence of screens when the alarm demonstration button 920 is activated (as opposed to the treatment sequence button 918). The medical device transitions to screen 928 responsive to the alarm demonstration button 920 being activated that displays one or more buttons that play an associated alert capable of being provided by the medical device. For example, the medical device may employ two types of audible alerts and the screen 928 may include a first button that causes the medical device to issue the first type of audible alert and a second button that causes the medical device to issue the second type of audible alert.

Figure 10:
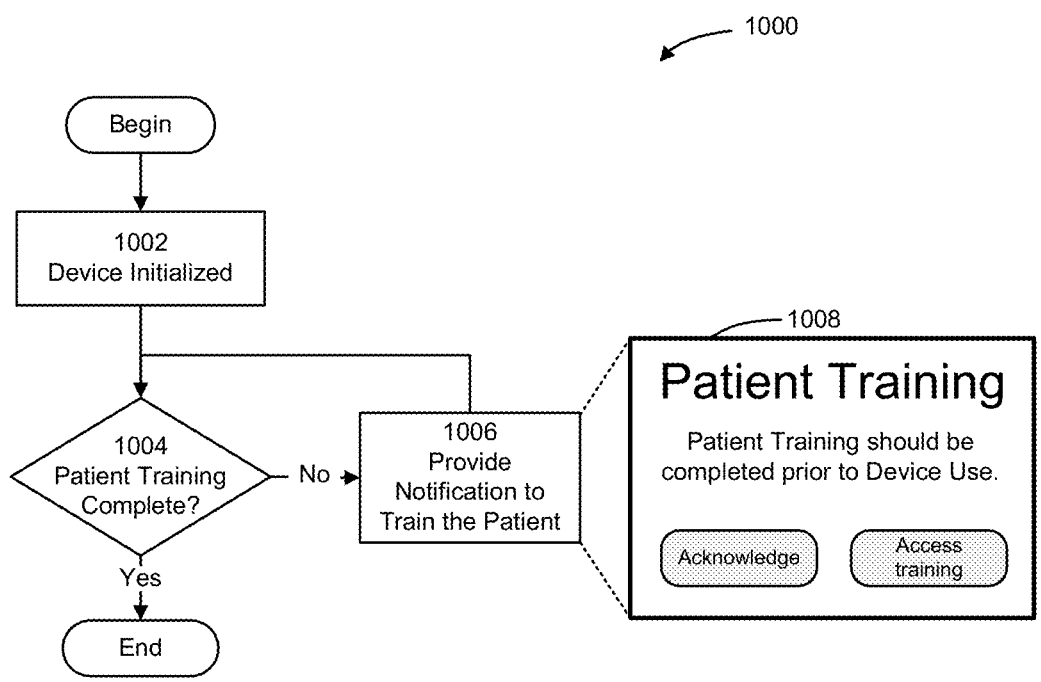
FIG. 10 shows an example process for reminding a caregiver to administer training to a patient.

Nurses and other caregivers in a busy hospital environment may outfit patients with a medical device without giving the patients adequate training. For example, a patient may not be trained on how to appropriately respond to certain device alerts and/or do things that are required of them in the event of the alert. FIG. 10 illustrates an example process 1000 to remind the caregiver to provide training to the patient.

In act 1002, the medical device determines that the device has been initialized. In some implementations, the medical device may determine that the device has been initialized by detecting, for example, the connector 510 being plugged into the port 202 of the controller 120, the initiation of communication between one or more sensing devices (e.g., sensing component 502) and the controller 120, a battery 212 being inserted into and/or connected to the controller 120, a predetermined period of time elapsing, and/or the medical device being fitted to the patient. The medical device may also determine that the device has been initialized by detecting that the setup screens for the medical device (e.g., screens 602-617 in FIGS. 6A and 6B) have been accessed by the caregiver.

In act 1004, the medical device determines whether user training was completely administered. For example, the device can be configured to require that one or more patient training modules be completed (e.g., by the caregiver administering the training to the patient) prior to deployment of the medical device on the patient. In some cases, the device can be configured to require that one or more caregiver training modules also be completed prior to deployment of the medical device.

For instance, in the event of a software update or a new feature release, it may be desirable that the caregiver be trained on the new device update or feature. As an example, after the device update or feature is installed, the device can issue a notification relating to the training on the update or feature. In some examples, a user of the device can be monitored for, e.g., abuse and/or compliance with device use guidelines. For instance, if a device abuse event is detected (e.g., the device perceives an impact exceeding a threshold), the device can issue a notification relating to a training module on device use and/or care. For instance, if the device detects that a device is being misused, e.g., a connector from the electrodes to the device is being improperly inserted, the device can automatically issue a notification relating to a training module on correct device use, e.g., in this case, correct inserting of the connector to the device.

Other device use events that can trigger training notifications as described herein include, for example, disconnecting the electrode connector when the device is active and/or prior to the device being turned off, improper battery insertion attempt(s), improper battery change event(s), incorrect sensing electrode(s) placement on the body of the patient, incorrect treatment electrode(s) placement on the body of the patient, incorrect treatment parameters being entered for the patient, and improper or incorrect user input.

For example, an improper battery change event can include determining that the device battery is approaching a predetermined amount of remaining battery charge (e.g., 15% or other preconfigured default or user configured level of charge). For example, incorrect sensing electrode placement can be automatically sensed by detecting whether an appropriate ECG signal of the patient is being detected. For example, incorrect treatment electrode placement can be automatically sensed by detecting a test signal (e.g., an electrode falloff signal) that is sent through the patient's body is received at a receiver configured to detect for such a signal. For example, such a test signal can be configured to have a predetermined frequency (e.g., in MHz range) such that the receiver can detect the signal.

For example, the incorrect treatment parameters or improper user input event can be in the form of one or more values being entered into the device setup screen corresponding to the patient treatment protocol that are incorrect. For instance, if a physician or other caregiver attempts to enter a shock energy value for a treatment pulse that violates an established rule (e.g., the value is lower than a shock energy value assigned to a previous treatment pulse), the device can issue a training notification or alert prompting that the caregiver complete a treatment protocol training session to ensure that correct shock energy values are being entered for the patient. Other improper and/or incorrect user input events can include pressing the response button(s) when there is no need for any response button actuation, pressing one or more user interface buttons at inappropriate times, and/or attempting to cause data transfer to the base station during an inappropriate time (e.g., when the device does not need to send any data to the base station).

For example, the device may cause the notification to be issued on detecting a number of such device abuse and/or improper use events in excess of a predetermined threshold. For instance, in the case of improper electrode placement, if an incorrect or improper ECG signal is received after three electrode placement attempts, the device can automatically issue the training notification. Similarly, if the device may not issue the training notification relating to a battery change event until it has detected three or more such infractions. For instance, the threshold number of events that initiate the training notification can be a preconfigured default value or user configurable by a user with the appropriate authorization and access level.

In some examples, the training notification may be in the form of an animation graphically displaying proper electrode placement on the body of the patient. Such an animation may continue to play in a loop until either a correct ECG signal is detected and/or the caregiver initiates the appropriate training module. In some examples, the training notification screen may not be dismissed or closed without completing the training module as described below. In some examples, the caregiver may temporarily suppress the notification for a period time (e.g., 10 minutes or other preconfigured default or user-defined amount of time) until such time the caregiver completes the training module. In some examples, the caregiver may be required to enter security credentials to temporarily suppress the notification. In some cases, the caregiver may only be able to temporarily suppress the notification without providing security credentials, but may be able to provide his or her security credentials and turn off all future notifications regarding the training module.

If the device does not detect completion of the one or more required training modules as noted below, the device can be configured to issue a notification to the caregiver. For example, the notification can be in the form of a "training required" or "training reminder" screen. For example, device can cause the notification screen can be configured to receive user input (e.g., via a user interface button on the screen) and, responsive to the input, cause the corresponding training module to be initiated.

In some implementations, the medical device can track progress through the training modules for detecting completion in the following manner. The medical device may, for example, track the screens displayed and/or the training modules accessed by the caregiver. The medical device may determine that the caregiver has completed patient training responsive to, for example, the number of completed training modules and/or displayed training screens transgressing a minimum threshold. It is appreciated that the duration of access to each of the training modules and/or screens may be monitored to reduce the risk of a caregiver attempting to rush through the training. For example, each module may have an associated minimum duration of access that may be dependent upon the length of the training module. For example, in a training module relating to device case, the device can be configured to ensure that the patient reviews each screen for at least 10 seconds (or other preconfigured default or user-defined amount of time) before proceeding to a next screen. The medical device may determine that a training module has been completed responsive to the medical device displaying the training module for at least the specified minimum amount of time. In another example, the medical device may monitor the number of screens and/or training module sections within a training module have been viewed and indicate that the training module is complete responsive to the number of screens accessed in the training module transgresses a minimum threshold.

For example, the device may be configured to determine that the training module is complete if at least 80% of screens within a training module have been reviewed. In another example, the device may be configured to deem the training module complete only if 100% of the screens have been reviewed. For instance, a particular training module, such as, how to press the response buttons in response to an alert condition may be viewed as an important training module and as such for this particular module, the device can be configured to require that all screens of the module are reviewed.

In some examples, the training module can include a quiz or an example simulation of a device alarm condition to confirm the user's (e.g., in this case, the patient's) understanding of device features. For instance, the device can prompt the patient to respond to a simulated condition involving an alarm scenario to test the patient's understanding of the device response mechanism.

In some implementations, the device can be configured to require user input to progress from one screen to the next within a training module to confirm that a screen has been reviewed prior to displaying a next screen. In some implementations, if no user input is received within a predetermined amount of time, e.g., 2 minutes, the device may deem the training module as being aborted and exit the module. In some cases, the training module can be reset to an initial screen of the training module in the absence of user input for the predetermined amount of time.

In various implementations, one or more of the thresholds or parameters described above can be set to default values, and be modified by a user with an appropriate access level and security credentials as described above.

If the medical device controller determines that the patient training has not been completed, the medical device may proceed to act 1006 and provide a notification to the caregiver as illustrated by patient training notification 1008. The patient training notification 1008 may remind the caregiver of the important of administering the training modules to the patient prior to use of the device by the patient. The patient training notification 1008 may include an acknowledge button (as illustrated) for the caregiver to temporarily silence the notification. In some examples, the patient training notification 1008 may include an indication of a suggested training to complete. For example, the medical device may determine that the patient treatment sequence training module was not completed and indicate in the patient training notification 1008 that the patient treatment sequence training module needs to be completed. The medical device may periodically repeat act 1004 and access whether the training has been administered to the patient and repeat act 1006 of providing the notification 1008 until the caregiver appropriately administers the training modules to the patient. In some implementations, the patient training notification 1008 may include an "Access training" button to allow the user to access the required training directly from the notification screen.

In some examples, the medical device may transmit a message to an external entity (e.g., via a base station) responsive to the notification 1008 being displayed in act 1006 and/or the medical device detecting that one or more training modules were rushed in act 1004. For example, the medical device may send a message to a supervisor of the caregiver indicating that the caregiver has inappropriately attempted patient training and/or has repeatedly failed to train the patient on the medical device. For example, the medical device may maintain a log of such information for later review.

It is appreciated that other training modules may be included in the medical device controller that may be directed to the caregiver, patient, and/or bystander personally. For example, the medical device may include a hospital based medical device and include a showering training module to train the caregiver on the appropriate procedure to shower the patient with the medical device. The showering training module may indicate, for example, that the medical device should be removed from the patient prior to showering. The medical device controller may further include a medical device care training module to train the caregiver and/or the patient on the appropriate procedure to care for the medical device while it is in use. For example, the medical device care training module may indicate that the batteries and/or the electrodes need to be changed periodically. These training modules may be made available to the caregiver in hospital based medical devices via, for example, the training menu screen 906. Other example training modules include, for example, a response button training module, a garment training module, a device action training module, a pacing training module, a defibrillation training module, and/or an arrhythmia detection training module.

The medical device may issue one or more notifications to remind the appropriate individual (e.g., the patient, the caregiver, and/or a bystander) of the appropriate procedures to interact with the medical device. The notifications may be triggered by various events. For example, the medical device may detect that a predetermined amount of time has passed since the last time a particular training module was reviewed. In some examples, the medical device may issue a targeted training notification responsive to detecting misuse of the medical device. For example, the medical device may detect that one or more electrodes are improperly attached to the patient and provide a notification to review a training module regarding electrode attachment. In another example, the medical device may detect that the battery charge level is below a threshold and provide a notification to review a battery care training module and/or a notification that the battery charge level is low.

Medical Device Alerts

Patients in an in-hospital setting may not immediately call a caregiver when the medical device issues an alert or alarm stating, for example, that an arrhythmia has been detected and/or that therapeutic shocks have been provided to the patient. The patients may, for example, only push the response buttons in response to an arrhythmia notification. In such situations, the hospital staff may not find out about the arrhythmia event until several minutes, maybe even hours after the event has occurred. Accordingly, in some examples, the medical device provides a notification for the patient to call a caregiver in response to the detection of various events (e.g., an arrhythmia). In some implementations, the device can be configured to automatically transmit a notification to an appropriate caregiver station tasked with monitoring the patient's condition.

Figure 11A:
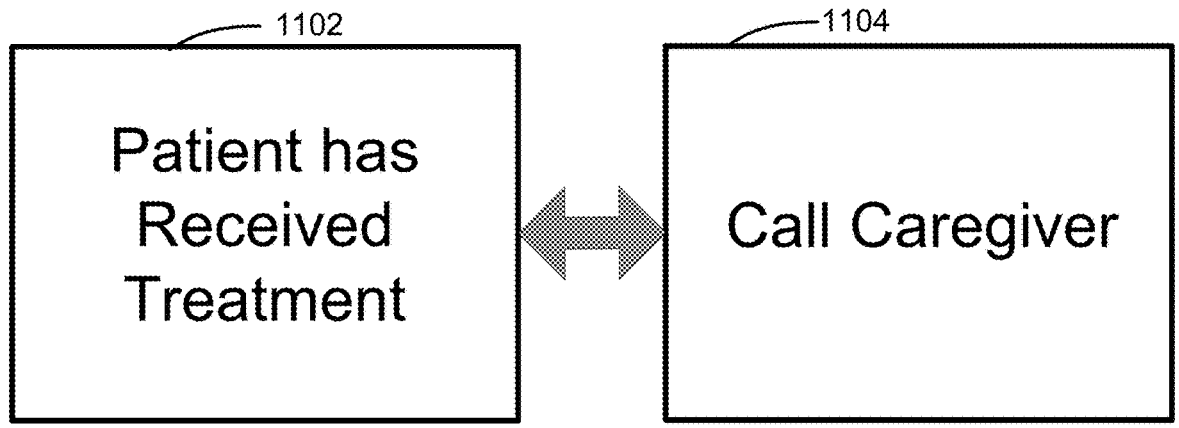
FIGS. 11A-11C show example alert messages displayed by a medical device in response to various events.
Figure 11B:
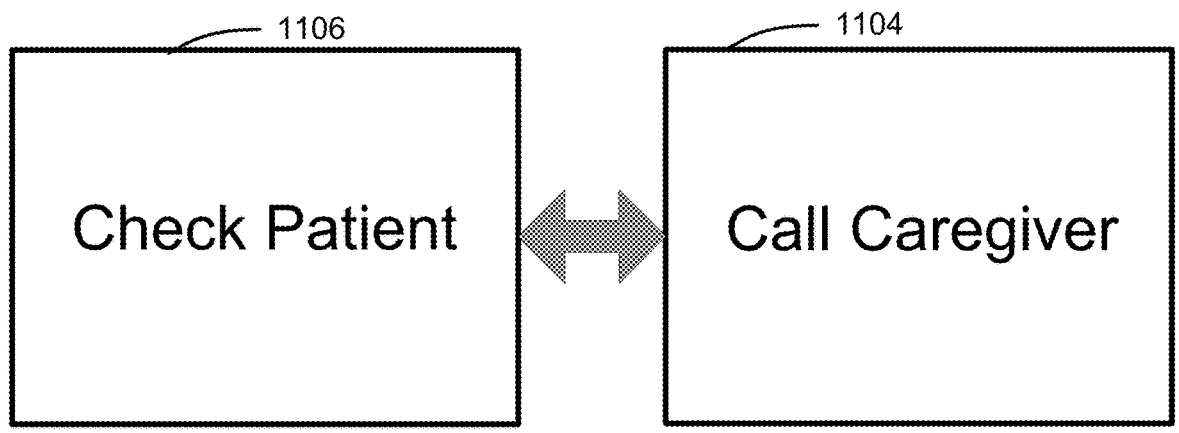
Figure 11C:
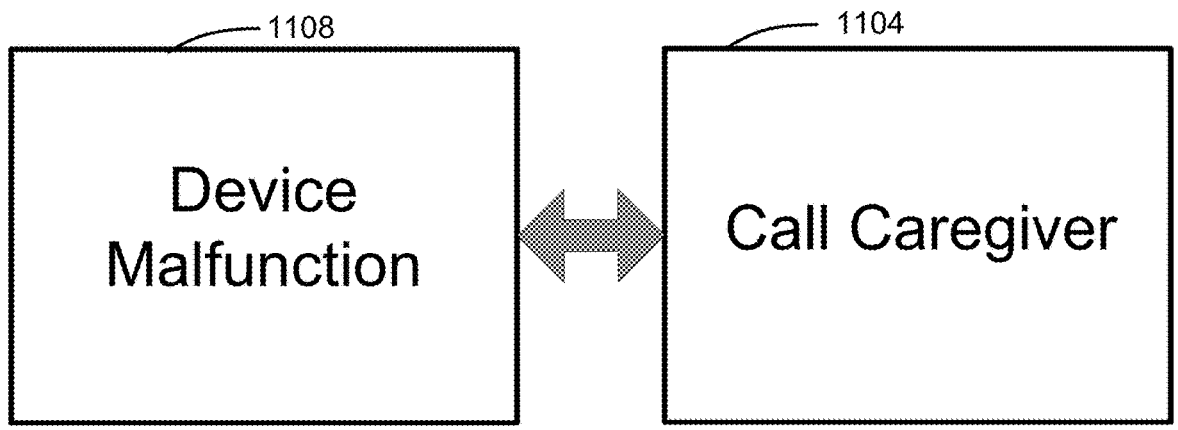

FIGS. 11A-11C illustrate example screens displayed by the medical device in response to various events alerting the patient to call a nurse or other caregiver and indicating, to the nurse or other caregiver, the event that has occurred and/or the appropriate action to take. Screens on the left of the page are directed to the caregiver, while screens on the right side of the page are directed to the patient. FIG. 11A, for example, illustrates the alternating screens displayed by the medical device in response to the patient receiving treatment. In screen 1104, the medical device instructs the patient (and potentially any bystanders) to call the nurse or other caregiver. The screen 1104 alternatives with screen 1102 notifying the nurse or other caregiver that the patient has received treatment. It is appreciated that the medical device may display alternating screens notifying the patient to call the nurse or other caregiver and notifying the nurse or other caregiver that the treatment is being delayed in response to a response button 210 being pushed as described above with reference to screens 910 and 912 in FIG. 9A.

FIG. 11B illustrates the alternating set of screens that may be displayed in response to the medical device determining, for example, that one or more therapeutic shocks have been provided to the patient and the heart rhythm of the patient has failed to return to a normal rhythm. The medical device alternate between a call caregiver screen 1104 and a check patient screen 1106 to indicate that the nurse or other caregiver should check the condition of the patient.

FIG. 11C illustrates the alternating set of screens that may be displayed in response to the medical device detecting a device malfunction. For example, the medical device may perform one or more self-tests of various internal components and determine that one or more components have failed the self-test. The medical device may alternate between a call caregiver screen 1104 and a device malfunction screen 1108. In some implementations, the medical device may identify the particular device malfunction detected to help the nurse or other caregiver troubleshoot the problem with the medical device.

In some examples, the medical device may issue an alert (e.g., via the base station) each time the call caregiver screen 1104 is displayed. For example, the medical device may issue an alert to a nursing station including an indication of issue and/or the location of the patient (e.g., room number). The alert may also indicate a degree of urgency of the issue. For example, the alert may indicate that the issue is very urgent when a patient arrhythmia is detected and less urgent when a minor malfunction of the medical device is detected.

Figure 12A:
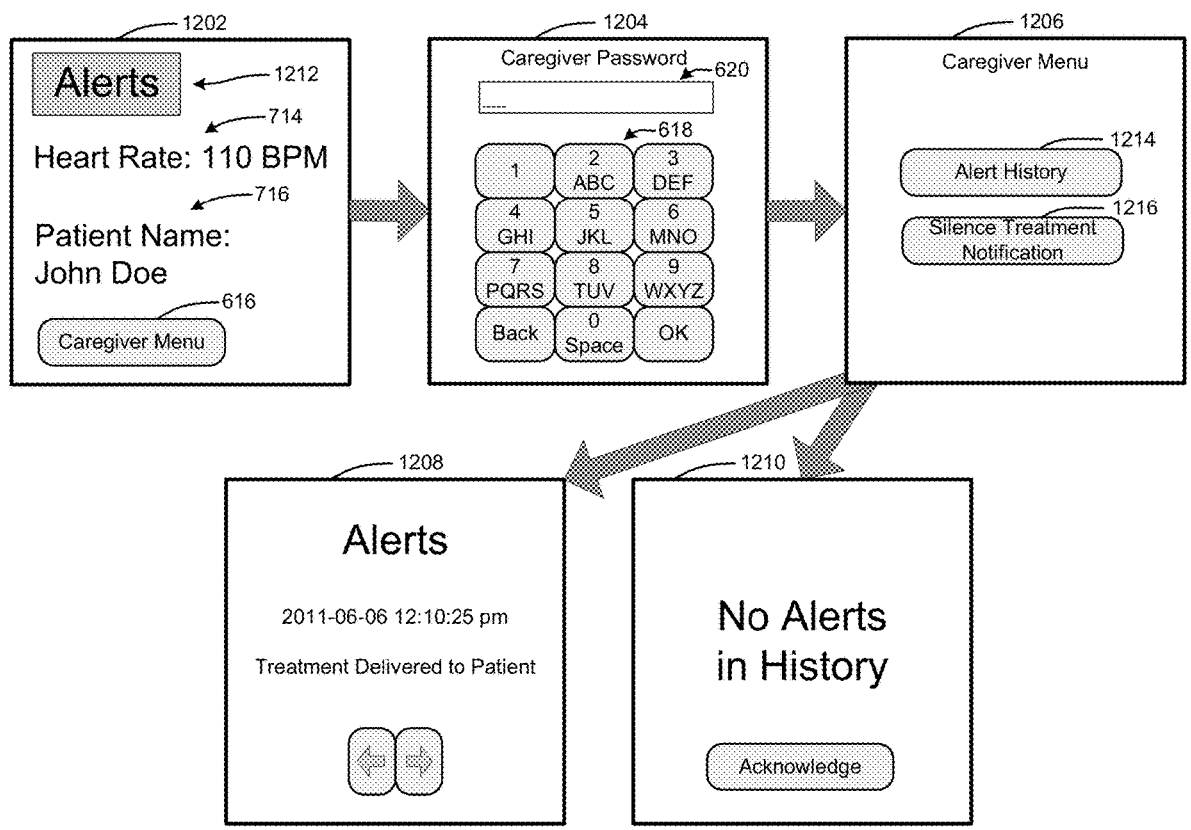
FIGS. 12A and 12B shows an example set of screens to manage the alerts on the medical device.
Figure 12B:
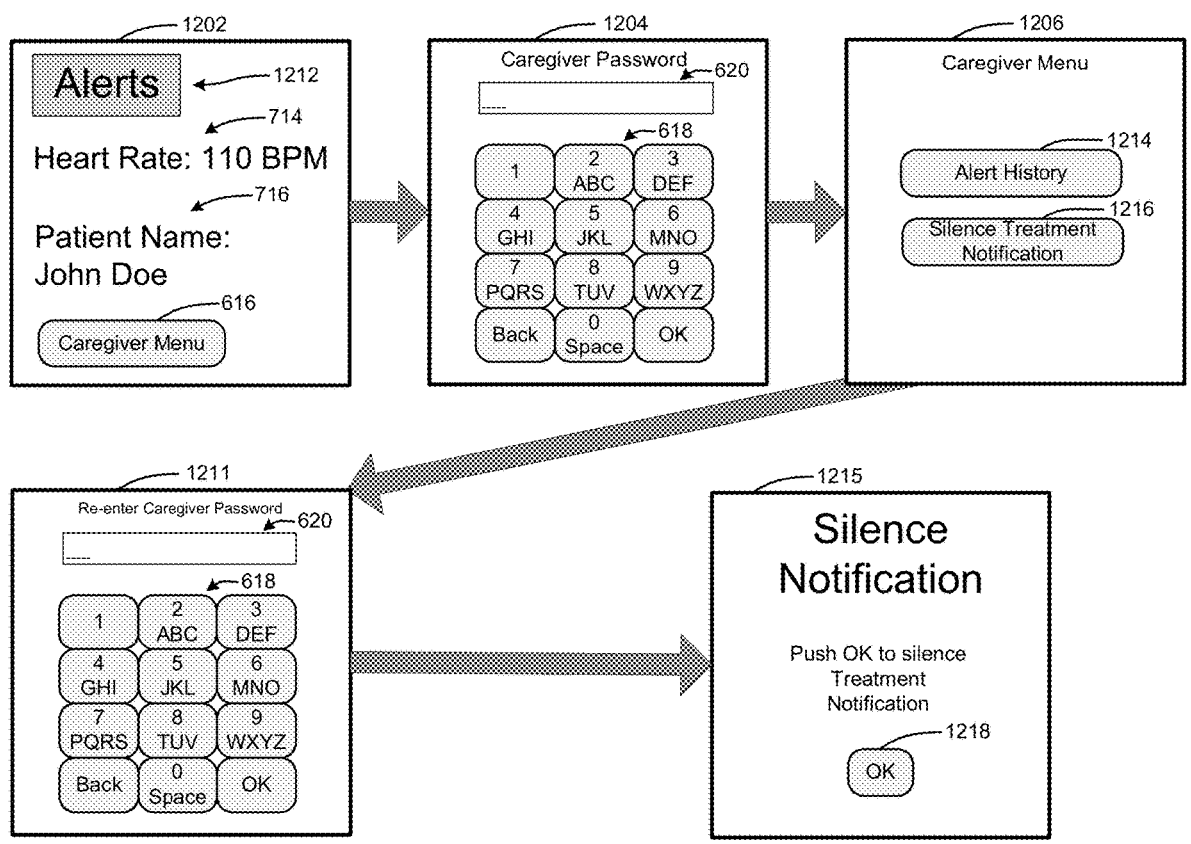

The medical device may track the alerts issued and allow a caregiver to silence one or more alerts. As noted above, for example, the caregiver may be permitted to silence the alert only after entering his/her security credentials. The alerts may be tracked locally by the medical device and/or sent to a remote server to be tracked for later access by various medical personnel. FIGS. 12A and 12B illustrate an example set of screens to allow a caregiver to view the alert history and silence a treatment notification on the medical device.

Referring to FIG. 12A, the home screen 1202 adds an indication of a recent alert 1212 to previous home screens described above (e.g., home screen 702 in FIGS. 7A-7D) responsive to the medical device issuing an alert. The medical device may provide access to a caregiver menu in screen 1206 to view the alert history and/or silence a treatment notification responsive to receiving an appropriate caregiver password in screen 1204. The caregiver menu in screen 1206 includes an alert history button 1214 and a silence treatment notification button 1216. The medical device transitions to screen 1208 responsive to activation of the alert history button 1214 and the medical device having one or more alerts stored in memory. Screen 1208 provides an indication of the various alerts to the caregiver. If the medical device does not have any alerts stored in the history, the medical device proceeds to screen 1210 and displayed a notification that there are no alerts in the history.

In FIG. 12B, first three screens 1202, 1204, and 1206 are similar to the screens with like reference numbers in FIG. 12A. FIG. 12B illustrates the sequence of screens responsive to the silence treatment notification button 1216 being activated (as opposed to the alert history button 1214) where the medical device transitions to screens 1211. In the example implementation of FIG. 12B, screen 1211 requires the caregiver to re-enter his/her security credential, and screen 1215 provides a notification to the caregiver that the notification may be silenced once the OK button 1218 is activated.

Service Device Alerts

Personnel in a busy health care facility may not know when a device needs to be serviced, or when to return a device to a service technician for tests/updates and/or other servicing needs. For example, it may be desirable that the medical device be serviced at periodic or substantially periodic points in time, or sent to a service center for such servicing. For instance, the device may track an amount of time since the device was last serviced in the form of a service clock. When the device reaches a predetermined service time threshold, for example, the device can issue a service reminder notification. For example, the predetermined service time threshold can be preconfigured to a default value of 6 months. In some implementations, after the device has been serviced a certain amount of times (e.g., at least 6 times), the predetermined default value may be automatically changed to a shorter or longer period of time (e.g., 9 months). Further, after performing service on the device, the service technician may access a device screen to reset the service reminder notification thus resetting the service clock. In some examples, the predetermined service time threshold may be manually set to a different value by an authorized user as depicted in FIG. 13.

Figure 13:
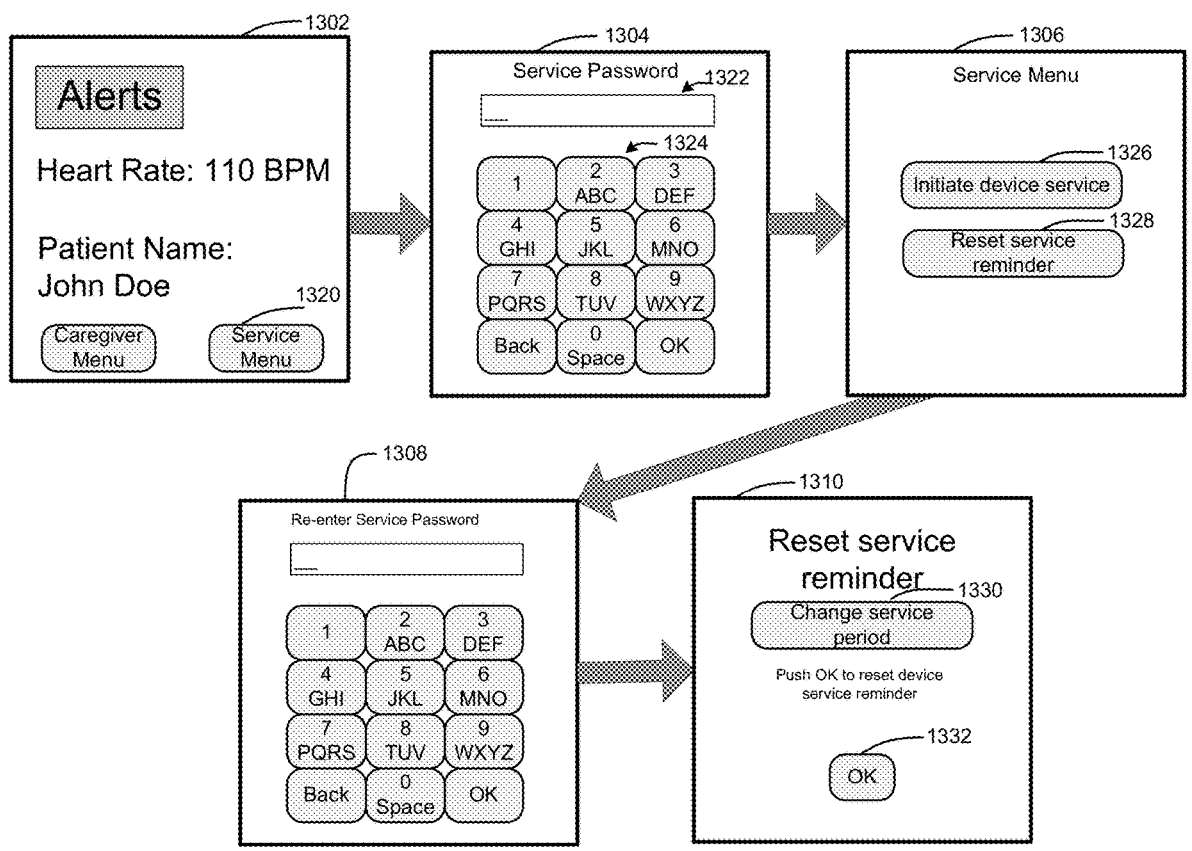
FIG. 13 shows an example set of screens to manage device service reminders.

As shown in FIG. 13, in some implementations, a service menu may be accessed. For example, the service menu may be accessed via a service menu button 1320 accessed via a home screen 1302. In some examples, the service menu may be accessed by a preconfigured unique user input, e.g., pressing and releasing one or more response buttons a predetermined amount of times (e.g., 10 times) in successive intervals not exceeding a preset threshold (e.g., 1 second), or pressing and holding one or more of the buttons a predetermined amount of time (e.g., 30 seconds). Other manner of input may also be provided for accessing the service menu.

In some examples, prior to providing access to the service menu the device may prompt the user to enter a enter service password on service password screen 1304, and provide an area 1322 for password entry and a corresponding keypad 1324. When the service menu 1306 is displayed, the user can perform one or more software service actions, e.g., by pressing the initiate device service 1326 button.

In some examples, the user can reset the service reminder by pressing the reset service reminder button 1328. The user may be prompted to re-enter his/her password on screen 1308 prior to accessing screen 1310 to reset the service reminder. In some implementations, the user may wish to change a service period for when the device needs to be next serviced. For example, the device may need to be serviced every 6 months and as such a default service period can be 6 months. However, after a certain number of servicing events, the user may set the service period to a shorter or longer period of time, e.g., 9 months.

Each of the processes and/or sequence of screens disclosed herein depicts one particular sequence of acts or screens in a particular example. The acts and/or screens included in each of these processes and/or sequences of screens may be performed by, or using, a medical device specially configured as discussed herein. Some acts and/or screens are optional and, as such, may be omitted in accord with one or more examples. Additionally, the order of acts and/or screens can be altered, or other acts can be added, without departing from the scope of the systems and methods discussed herein.

The examples of the methods and apparatuses discussed herein are not limited in application to the details of construction and the arrangement of components set forth in the above description or illustrated in the accompanying drawings. The methods and apparatuses are capable of implementation in other examples and of being practiced or of being carried out in various ways. Examples of specific implementations are provided herein for illustrative purposes only and are not intended to be limiting. In particular, acts, elements and features discussed in connection with any one or more examples are not intended to be excluded from a similar role in any other examples.

As noted herein, the external medical device can be used in conjunction with a patient in a health care facility environment or setting. For instance, such environments can include those where a patient is being cared for including hospices, elder care facilities, assisted living facilities, long term care facilities, rehabilitation centers, healthcare clinics, mobile clinics, emergency response vehicles, and outpatient medical clinics. Further, the device as described herein can be used in any setting/environment where such devices may be used such as within office spaces and buildings, public areas and buildings, personal home settings, and private business areas and buildings. Moreover, in various implementations, the external medical device may be used on an outpatient basis, e.g., in connection with patients that are at home or are performing their everyday activities at home, work, or elsewhere. In some cases, the external medical device can be used in conjunction with a patient receiving at-home medical care.

In implementations where example numerical values are provided (e.g., as a predetermined numerical value), it should be understood that such values can be set through one or more user-configurable parameters. For example, the example numerical value can be provided as a default value, and a technician or a caregiver (such as a nurse or physician) can modify the values in accordance with the principles described herein through a user interface.

Having thus described several aspects of at least one example of this disclosure, it is to be appreciated various alterations, modifications, and improvements will readily occur to those skilled in the art. Such alterations, modifications, and improvements are intended to be part of this disclosure, and are intended to be within the scope of the disclosure. Accordingly, the foregoing description and drawings are by way of example only.

What is claimed is:

1. An external wearable medical device comprising:
   at least one electrode configured to detect cardiac activity of a patient;
   at least one therapy electrode configured to provide a therapy to the patient in response to detecting an arrhythmia event in the patient based at least in part on the detected cardiac activity;
   a graphical user interface display disposed on the external wearable medical device and comprising at least one caregiver interface and at least one patient interface; and
   at least one processor in communication with the graphical user interface display, wherein the at least one processor is configured to
   provide a first set of information to the at least one caregiver interface, wherein the first set of information comprises information for operating the external wearable medical device in conjunction with the patient and an alert history of the wearable medical device including an indication of the detected arrhythmia event in the patient, provide a second set of information to the at least one patient interface, wherein the second set of information comprises information for allowing the patient to cause the external wearable medical device to suspend providing the therapy to the patient, and wherein the second set of information further comprises a direction to the patient to contact a caregiver responsive to detecting an event affecting at least one of the external wearable medical device and the patient, and responsive to detecting the event affecting at least one of the external wearable medical device and the patient, automatically transmitting a notification of the event to an external entity.

2. The external wearable medical device of claim 1, wherein the external entity is a caregiver station monitoring a condition of the patient.

3. The external wearable medical device of claim 1, wherein the external entity is a base station configured to issue alerts to medical personnel.

4. The external wearable medical device of claim 1, wherein the notification of the event includes an indication of at least one of a type of the event, a location of the patient, and an urgency of the event.

5. The external wearable medical device of claim 1, wherein the event affecting at least one of the external wearable medical device and the patient includes at least one of electrode falloff, excessive noise, and low battery.

6. The external wearable medical device of claim 1, wherein the event affecting at least one of the external wearable medical device and the patient comprises the detected arrhythmia event in the patient.

7. The external wearable medical device of claim 6, wherein the detected arrhythmia event comprises at least one of a ventricular tachycardia event, a ventricular fibrillation event, a bradycardia event, and an atrial fibrillation event.

8. The external wearable medical device of claim 1, wherein the graphical user interface display further comprises at least one service interface, wherein the at least one processor is further configured to provide a third set of information to the at least one service interface, wherein the third set of information comprises information for allowing a service technician to access device settings not accessible by the patient.

9. The external wearable medical device of claim 1, wherein the information for operating the external wearable medical device comprises at least one training module.

10. The external wearable medical device of claim 9, wherein the at least one training module comprises at least one of a patient training module and a caregiver training module.

11. The external wearable medical device of claim 9, wherein the at least one training module comprises a response button training module, a garment training module, and a device action training module.

12. The external wearable medical device of claim 9, wherein the first set of information comprises at least one of a direction to the caregiver to administer the at least one training module to the patient and a direction to the caregiver to review the at least one training module.

13. The external wearable medical device of claim 1, wherein the at least one processor is configured to provide access to a user with a caregiver level access to modify a treatment protocol of the patient.

14. The external wearable medical device of claim 1, wherein the at least one processor is configured to provide access to a user with patient level access to a limited set of allowed interactions.

15. A method of operating an external wearable medical device comprising:

monitoring ECG information of a patient, the ECG information obtained from at least one ECG sensing electrode of the external wearable medical device;

providing, on a graphical user interface display disposed on the external wearable medical device, a first set of information in at least one caregiver interface, wherein the first set of information comprises information for operating the external wearable medical device in conjunction with the patient and an alert history of the external wearable medical device including an indication of any detected arrhythmia events in the patient, providing, on the graphical user interface display, a second set of information in at least one patient interface, wherein the second set of information comprises information for allowing the patient to cause the external wearable medical device to suspend providing a therapy to the patient, and wherein the second set of information further comprises a direction to the patient to contact a caregiver responsive to detecting an event affecting at least one of the external wearable medical device and the patient, and responsive to detecting the event affecting at least one of the external wearable medical device and the patient, automatically transmitting a notification of the event to an external entity.

16. The method of claim 15, wherein the notification of the event includes an indication of at least one of a type of the event, a location of the patient, and an urgency of the event.

17. The method of claim 15, wherein the event affecting at least one of the external wearable medical device and the patient includes at least one of electrode falloff, excessive noise, and low battery.

18. The method of claim 15, wherein the event affecting at least one of the external wearable medical device and the patient comprises the detected arrhythmia event in the patient.

19. The method of claim 18, wherein the detected arrhythmia event comprises at least one of a ventricular tachycardia event, a ventricular fibrillation event, a bradycardia event, and an atrial fibrillation event.

20. The method of claim 15, wherein the external entity is a caregiver station monitoring a condition of the patient.

* * * * *